United States Patent
Join et al.

(10) Patent No.: US 10,980,727 B2
(45) Date of Patent: Apr. 20, 2021

(54) MIXTURES CONTAINING (E)-3-BENZO[1,3]DIOXOL-5-YL-N,N-DIPHENYL-2-PROPENAMIDE

(71) Applicant: SYMRISE AG, Holzminden (DE)

(72) Inventors: Benoit Join, Holzminden (DE); Michael Backes, Holzminden (DE); Arnold Machinek, Holzminden (DE); Ulrike Simchen, Holzminden (DE); Jenny Weissbrodt, Holzminden (DE); Jens Fahle, Detmold (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 16/324,166

(22) PCT Filed: Aug. 9, 2016

(86) PCT No.: PCT/EP2016/068978
§ 371 (c)(1),
(2) Date: Feb. 8, 2019

(87) PCT Pub. No.: WO2018/028770
PCT Pub. Date: Feb. 15, 2018

(65) Prior Publication Data
US 2019/0167553 A1 Jun. 6, 2019

(51) Int. Cl.
| | | |
|---|---|---|
| *A61K 8/42* | (2006.01) | |
| *A61K 8/92* | (2006.01) | |
| *A61K 8/34* | (2006.01) | |
| *A61K 8/37* | (2006.01) | |
| *A61Q 5/02* | (2006.01) | |
| *A61Q 19/10* | (2006.01) | |
| *A61Q 19/00* | (2006.01) | |

(52) U.S. Cl.
CPC .......... *A61K 8/42* (2013.01); *A61K 8/34* (2013.01); *A61K 8/37* (2013.01); *A61K 8/922* (2013.01); *A61Q 5/02* (2013.01); *A61Q 19/004* (2013.01); *A61Q 19/10* (2013.01); *A61K 2800/244* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 7,727,516 B2 * | 6/2010 | Botchkareva | A61P 17/00 424/74 |
| 8,927,605 B2 * | 1/2015 | Subkowski | A61P 25/04 514/617 |
| 2004/0082654 A1 * | 4/2004 | Pesce | A61K 8/37 514/547 |
| 2012/0263659 A1 | 10/2012 | Subkowski et al. | |

FOREIGN PATENT DOCUMENTS

| | | |
|---|---|---|
| EP | 2423290 A1 | 2/2012 |
| EP | 2824157 A1 | 1/2015 |
| JP | 2013511270 A | 4/2013 |
| RU | 2013125846 A | 12/2014 |
| WO | 2011061330 A2 | 5/2011 |
| WO | WO-2011/061330 A2 | 5/2011 |

OTHER PUBLICATIONS

Google patent search_Apr. 7, 2020_triethyl citrate and peppermint oil cooling (Year: 2020).*
Russian Office Action and English translation dated Dec. 24, 2019 for corresponding Russian Application No. 2019106481.
International Search Report and Written Opinion dated Oct. 24, 2016 for corresponding PCT Application No. PCT/EP2016/068978.
European Office Action dated Jul. 8, 2020 for corresponding European Application No. 16750164.2.
Japanese Office Action dated Jul. 13, 2020 for corresponding Japanese Application No. 2019-507145.

* cited by examiner

*Primary Examiner* — Michael P Cohen
(74) *Attorney, Agent, or Firm* — Polsinelli PC

(57) ABSTRACT

Mixtures comprising a selected cooling active ingredient (E)-3-benzo[1,3]dioxol-5-yl-N,N-diphenyl-2-propenamide and at least one other substance which acts as a solvent for (E)-3-benzo[1,3]dioxol-5-yl-N,N-diphenyl-2-propenamide, wherein the substance is selected form the group consisting of benzyl benzoate, diethyl succinate, triethyl citrate, triacetin, ethanol, peppermint oil, anethol, optamint, propylene glycol, further cooling active ingredients or mixtures thereof.

6 Claims, No Drawings

MIXTURES CONTAINING (E)-3-BENZO[1,3]DIOXOL-5-YL-N,N-DIPHENYL-2-PROPENAMIDE

CROSS-REFERENCE TO RELATED APPLICATIONS

This application is a national stage application (under 35 U.S.C. § 371) of PCT/EP2016/068978, filed Aug. 9, 2016, which is incorporated herein by reference in its entirety.

FIELD OF THE INVENTION

The invention relates to the field of mixtures comprising a selected cooling substance (E)-3-benzo[1,3]dioxol-5-yl-N,N-diphenyl-2-propenamide and at least one further substance acting as a solvent for (E)-3-benzo[1,3]dioxol-5-yl-N,N-diphenyl-2-propenamide, wherein the substance is selected from the group consisting of benzyl alcohol, 2-phenyl ethanol, benzyl benzoate, diethyl succinate, triethyl citrate, triacetin, ethanol, peppermint oil, anethol, optamint, propylene glycol, further cooling substances or mixtures thereof.

BACKGROUND ART (E)-3-benzo[1,3]dioxol-5-yl-N,N-diphenyl-2-propenamide is known by the CAS No. 1309389-73-8 and by the trade name iCool®MC6 of the company Symrise AG. The substance is a solid which was developed as new cooling substance. In WO 20011/061330, the use of (E)-3-benzo[1,3]dioxol-5-yl-N,N-diphenyl-2-propenamide as a modulator of the cold and menthol receptor TRPM8 is disclosed. Also, the application of the cooling substance in different formulations such as mouthwash, toothpaste, chewing gums etc. is disclosed.

To exploit and optimise the cooling effect of (E)-3-benzo[1,3]dioxol-5-yl-N,N-diphenyl-2-propenamide, as well as ensuring an easier processing into aromas and semi-finished products, the substance must be converted into a solution before processing. However, the solubility of (E)-3-benzo[1,3]dioxol-5-yl-N,N-diphenyl-2-propenamide is in several cases not sufficient, causing problems for storage, further processing and handling.

The object of the present invention was thus to find suitable solvents or, respectively, solvent systems for (E)-3-benzo[1,3]dioxol-5-yl-N,N-diphenyl-2-propenamide (herein abbreviated as BDDPA). Particularly, it was the object of the invention to provide solvents and solvent systems for (E)-3-benzo[1,3]dioxol-5-yl-N,N-diphenyl-2-propenamide, in which (E)-3-benzo[1,3]dioxol-5-yl-N,N-diphenyl-2-propenamide can be stably stored in a dissolved condition. A partial problem was to provide suitable solvents and combinations thereof, in which particularly more than 2 wt.-%, preferably more than 5 wt.-% of (E)-3-benzo[1,3]dioxol-5-yl-N,N-diphenyl-2-propenamide are maintained solved, particularly preferably at 23° C. A further partial problem was, particularly for the production of semi-finished products, to develop solvents or, respectively, solvent systems, in which (E)-3-benzo[1,3]dioxol-5-yl-N,N-diphenyl-2-propenamide is present in a dissolved condition and which remain stable at higher temperatures, preferably in a range of from 60° C. to 80° C., until further processing.

DESCRIPTION OF THE INVENTION

A first object of the invention relates to a mixture comprising or consisting of or substantially consisting of (a) (E)-3-benzo[1,3]dioxol-5-yl-N,N-diphenyl-2-propenamide and
(b) at least one substance selected from the group consisting of benzyl alcohol, 2-phenyl ethanol, benzyl benzoate, diethyl succinate, triethyl citrate, triacetin, ethanol, peppermint oil, anethol, optamint, propylene glycol, further cooling substances or mixtures thereof.

It was surprisingly found that the present mixture is stable and the cooling substance (E)-3-benzo[1,3]dioxol-5-yl-N,N-diphenyl-2-propenamide can be variably maintained in a stably dissolved condition in a broad range, depending on the solvent or, respectively, combination of said solvents, of from 2 wt.-% to 20 wt.-% or, respectively, of from 5 wt.-% to 15 wt.-%.

Cooling Substances

Cooling substances in the meaning of the present invention, which may act as solvents for BDDPA, are preferably selected from the group consisting of menthol, menthyl methyl ether, menthone glyceryl acetal (Frescolat® MGA, FEMA GRAS 3807), menthone glyceryl ketal (FEMA GRAS 3808), menthyl lactate (Frescolat® ML, FEMA GRAS 3748), menthol ethylene glycol carbonate (Frescolat® MGC, FEMA GRAS 3805), menthol propylene glycol carbonate (Frescolat® MPC, FEMA GRAS 3806), menthyl-N-ethyloxamate (Frescolat®, Monomethyl Succinate (FEMA GRAS 3810), monomenthyl glutarate (FEMA GRAS 4006), menthoxy-1,2-propanediol (FEMA GRAS 3784), menthoxy-2-methyl-1,2-propandiol (FEMA GRAS 3849) as well as menthane carboxylic acid esters and amides as e.g. WS-3 (FEMA GRAS 3455), WS-5 (FEMA GRAS 4309), WS-12 (Frescolat® SC-1, FEMA GRAS 4681) and WS-23 (FEMA GRAS 3804) as well as mixtures thereof.

Optamint

Optamint is a mixture of more than 50 different natural essential oils and natural or nature identical flavouring substances. Optamints have variable compositions of different (partially fractioned) oils, which are preferably a mixture of for example different peppermint oils and spearmint oils as well as eucalyptus globulus oil, star anise oil, menthol, menthone, isomenthone, menthyl acetate, anethol, eucalyptol etc. A precise indication of the composition of optamints is thus not possible. The product series Optamint® is commercially available from the company Symrise AG.

In a preferred embodiment, benzyl alcohol or 2-phenyl ethanol or benzyl benzoate is used as solvent for BDDPA, benzyl alcohol is particularly suitable.

The use of benzyl alcohol or 2-phenyl ethanol or benzyl benzoate was shown to be advantageous to dissolve (E)-3-benzo[1,3]dioxol-5-yl-N,N-diphenyl-2-propenamide (BDDPA) and also obtain a stable solution for storage. Preferably, 2 wt.-% to 20 wt.-%, preferably 5 wt.-% to 15 wt.-% BDDPA can likewise be maintained stably in solution. Additionally, it was found that such a mixture is stable up to 100° C., preferably up to 90° C. Particularly preferred is benzyl alcohol.

It was further found to be advantageous to use solvent combinations for dissolving BDDPA. Particularly with regard to the subsequent application, a further step in the (final) step of production can be saved by using solvents which can also show an effect.

In a preferred embodiment, the solvent is thus a binary system of two substances as solvent for BDDPA, selected from the group consisting of benzyl alcohol, 2-phenyl ethanol, benzyl benzoate, diethyl succinate, triethyl citrate, triacetin, ethanol, peppermint oil, anethol, optamint, propylene glycol and further cooling substances as described above.

According to the invention, binary solvent combination of benzyl alcohol and a further substance selected from the group consisting of 2-phenyl ethanol, benzyl benzoate, diethyl succinate, triethyl citrate, triacetin, ethanol, peppermint oil, anethol, optamint, propylene glycol and further cooling substances as described above are particularly preferred.

Particularly preferred are binary solvent combinations or, respectively, mixtures comprising or consisting benzyl alcohol with a further solvent. Particularly preferred are the binary solvent combinations or, respectively, mixtures selected from Benzyl alcohol and 2-phenyl ethanol,
Benzyl alcohol and benzyl benzoate,
Benzyl alcohol and diethyl succinate
Benzyl alcohol and triethyl citrate,
Benzyl alcohol and triacetin,
Benzyl alcohol and ethanol,
Benzyl alcohol and peppermint oil,
Benzyl alcohol and anethol,
Benzyl alcohol and optamint,
Benzyl alcohol and propylene glycol,
Benzyl alcohol and menthol,
Benzyl alcohol and menthyl lactate (Frescolat® ML),
Benzyl alcohol and menthol propylene glycol carbonate (Frescolat® MPC),
Benzyl alcohol and menthol ethylene glycol carbonate (Frescolat® MGC),
Benzyl alcohol and menthone glyceryl acetal (Frescolat® MGA),
Benzyl alcohol and menthane carboxylic acid esters and amides.

Further, the following binary solvent combinations or, respectively, solvent mixtures are particularly preferred:

2-Phenyl ethanol and menthol propylene glycol carbonate (Frescolat® MPC),
Diethyl succinate and 2-phenyl ethanol,
Triacetin and benzyl benzoate,
Triethyl citrate and triacetin,
2-Phenyl ethanol and peppermint oil,
2-Phenyl ethanol and optamint,
Anethol and triacetin,
Peppermint oil and menthyl lactate (Frescolat® ML),
Triacetin and menthone glyceryl acetal (Frescolat® MGA
Optamint and menthyl lactate (Frescolat® ML),
Triethyl citrate and menthol ethylene glycol carbonate (Frescolat® MGC).

Preferred mixtures according to the invention thus essentially contain as solvent b) binary solvent combinations or, respectively solvent mixtures as described above.

Binary solvent mixtures according to the invention preferably have for example the following ratios:

i) 2-Phenyl ethanol and benzyl alcohol, preferably in a ratio of from 10.25:1 to 5:1,
ii) Diethyl succinate and 2-phenyl ethanol, preferably in a ratio of from 1:8 to 8:1,
iii) Triacetin and benzyl benzoate, preferably in a ratio of from 4:5 to 5:4,
iv) Benzyl benzoate and benzyl alcohol, preferably in a ratio of from 1:8 to 8:1,
v) Phenyl ethanol and benzyl benzoate of from 1:8 to 8:1.

The preferred binary solvent mixtures listed above, were found to be particularly good in their effect of solving BDDPA and variably maintain BDDPA stably solved in a broad range, depending on the solvent or, respectively, combination of said solvents in an amount of from 2 wt.-% to 20 wt.-%, preferably 5 wt.-% to 10 wt.-%. This has the advantage that BDDPA can thus be obtained in a variable amount suitable for the final formulation, such that the possible mixtures in which BDDPA is present in a dissolved condition, is rather broad. Additionally, such mixtures are stable up to 100° C., preferably up to 90° C.

Particularly, the solvent combination of benzyl alcohol and a further substance of group b) was particularly advantageous to achieve the effects as described above.

In a further preferred embodiment, the solvent or, respectively, solvent system for BDDPA is a ternary system od three solvents selected from the group consisting of benzyl alcohol, 2-phenyl ethanol, benzyl benzoate, diethyl succinate, triethyl citrate, triacetin, ethanol, peppermint oil, anethol, optamint, propylene glycol and further cooling substances.

Particularly preferred herein are ternary solvent combinations of benzyl alcohol and two further substances selected from the group consisting of 2-phenyl ethanol, benzyl benzoate, diethyl succinate, triethyl citrate, triacetin, ethanol, peppermint oil, anethol, optamint, propylene glycol and further cooling substances as described above.

Particularly preferred are ternary solvent combinations or, respectively, mixtures, which substantially contain or consist of benzyl alcohol with two further solvents, wherein the two further solvents are selected from the group consisting of 2-Phenyl ethanol and benzyl benzoate,
2-Phenyl ethanol and diethyl succinate,
Triethyl citrate and triacetin,
Triacetin and ethanol,
Triacetin and peppermint oil,
Menthol ethylene glycol carbonate (Frescolat® MGC) and anethol,
2-Phenyl ethanol and optamint,
Optamint and propylene glycol,
Diethyl succinate and menthol,
Triacetin and menthyl lactate (Frescolat® ML),
Anethol and menthol propylene glycol carbonate (Frescolat® MPC),
Triacetin and menthol ethylene glycol carbonate (Frescolat® MGC),
2-Phenyl ethanol and menthone glyceryl acetal (Frescolat® MGA),
2-Phenyl ethanol and menthane carboxylic acid esters and amides,
2-Phenyl ethanol and menthol propylene glycol carbonate (Frescolat® MPC),
Triacetin and benzyl benzoate,
2-Phenyl ethanol and peppermint oil,
Anethol and triacetin,
Peppermint oil and menthyl lactate (Frescolat® ML),
Triacetin and menthone glyceryl acetal (Frescolat® MGA),
Optamint and menthyl lactate (Frescolat® ML),
Triethyl citrate and menthol ethylene glycol carbonate (Frescolat® MGC).
Benzyl benzoate and menthol ethylene glycol carbonate (Frescolat® MGC),
2-Phenyl ethanol and triethyl citrate,
Triethyl citrate and diethyl succinate,
Peppermint oil and menthyl lactate (Frescolat® ML),
Ethanol and menthyl lactate (Frescolat® ML).

Further preferred are the following ternary solvent combinations or, respectively, solvent mixtures:

Triethyl citrate and triacetin menthyl lactate (Frescolat® ML),
Triacetin, 2-phenyl ethanol and peppermint oil, 2-Phenyl ethanol, optamint and peppermint oil,
2-Phenyl ethanol, triacetin and optamint,
Anethol, Benzyl alcohol and triacetin,
2-Phenyl ethanol and benzyl benzoate,
2-phenyl ethanol and diethyl succinate,
Triethyl citrate, triacetin and peppermint oil
Optamint, triacetin and ethanol,
Triacetin, menthol ethylene glycol carbonate (Frescolat® MGC) and anethol
2-phenyl ethanol, optamint and propylene glycol,
Diethyl succinate, triacetin and menthol,
Triacetin, benzyl benzoate and menthyl lactate (Frescolat® ML),
Anethol, menthol propylene glycol carbonate (Frescolat® MPC) and menthol ethylene glycol carbonate (Frescolat® MGC),
Triacetin, 2-phenyl ethanol and menthone glyceryl acetal (Frescolat® MGA),
Peppermint oil, 2-phenyl ethanol and menthane carboxylic acid esters and amides,
Triacetin, 2-phenyl ethanol and menthol propylene glycol carbonate (Frescolat® MPC),
Menthyl lactate (Frescolat® ML), 2-phenyl ethanol and peppermint oil,
Anethol, triacetin and menthone glyceryl acetal (Frescolat® MGA),
Optamint, benzyl benzoate and menthyl lactate (Frescolat® ML),
Benzyl benzoate, triethyl citrate and menthol ethylene glycol carbonate (Frescolat® MGC).

Ternary solvent mixtures according to the present invention preferably have the following ratios:
i) 2-Phenyl ethanol, benzyl alcohol and triethyl citrate, preferably in a ratio of from 10:1:15 to 5:1:3, or
ii) Triethyl citrate, benzyl alcohol and diethyl succinate, preferably in a ratio of from 4:1:7 to 7:1:4, or
iii) Triacetin, 2-phenyl ethanol and peppermint oil, preferably in a ratio of from 2:2:4 to 4:4:2.

The ternary solvent combinations and mixtures as above were found to be particularly good in solving BDDPA and variably maintain BDDPA in a dissolved condition, depending on the solvent or, respectively, combination of said solvents in an amount of from 2 wt.-% to 20 wt.-%, preferably 5 wt.-% to 10 wt.-%. This has the advantage that BDDPA can thus be obtained in an amount sufficient for the final formulation such that the such that the possible mixtures in which BDDPA is present in a dissolved condition, is rather broad. Additionally, such mixtures are stable up to 100° C., preferably up to 90° C.

In a further preferred embodiment, the solvent or, respectively, solvent system for BDDPA is a quarternary system of four solvents selected from the group consisting of benzyl alcohol, 2-phenyl ethanol, benzyl benzoate, diethyl succinate, triethyl citrate, triacetin, ethanol, peppermint oil, anethol, optamint, propylene glycol and further cooling substances.

Particularly preferred herein are quarternary solvent combinations of benzyl alcohol and three further substances selected from the group consisting of 2-phenyl ethanol, benzyl benzoate, diethyl succinate, triethyl citrate, triacetin, ethanol, peppermint oil, anethol, optamint, propylene glycol and further cooling substances as described above.

Particularly preferred are quarternary solvent combinations or, respectively, mixtures, which substantially contain or consist of benzyl alcohol with three further solvents, wherein the three further solvents are selected from the group consisting of 2-Phenyl ethanol, triethyl citrate and triacetin,
Peppermint oil, 2-phenyl ethanol and triethyl citrate,
Triethyl citrate, menthyl lactate (Frescolat® ML) and diethyl succinate
Triethyl citrate, triacetin and anethol,
2-Phenyl ethanol, triacetin, and optamint,
Peppermint oil, benzyl alcohol and menthyl lactate (Frescolat® ML),
Optamint, ethanol and menthyl lactate (Frescolat® ML),
2-Phenyl ethanol, benzyl benzoate and diethyl succinate,
Triethyl citrate, triacetin and ethanol,
Peppermint oil, anethol and optamint,
2-Phenyl ethanol, benzyl benzoate and propylene glycol,
2-Phenyl ethanol, benzyl benzoate and menthol propylene glycol carbonate (Frescolat® MPC),
Triethyl citrate, optamint and ethanol,
Triacetin, benzyl benzoate and menthoxy-2-methyl-1,2-propandiol,
Menthone glyceryl acetal (Frescolat® MGA), triacetin and anethol.

Further preferred are the following quarternary solvent combinations and solvent mixtures:
Anethol, triacetin, peppermint oil and menthol ethylene glycol carbonate (Frescolat® MGC)
Triacetin, ethanol, 2-phenyl ethanol and peppermint oil,
2-Phenyl ethanol, optamint, diethyl succinate and peppermint oil,
Anethol, 2-phenyl ethanol, benzyl alcohol and triacetin, The quarternary solvent combinations and mixtures as above were found to be particularly good in solving BDDPA and variably maintain BDDPA in a dissolved condition, depending on the solvent or, respectively, combination of said solvents in an amount of from 2 wt.-% to 20 wt.-%, preferably 5 wt.-% to 10 wt.-%. This has the advantage that BDDPA can thus be obtained in an amount sufficient for the final formulation such that the such that the possible mixtures in which BDDPA is present in a dissolved condition, is rather broad. Additionally, such mixtures are stable up to 100° C., preferably up to 90° C.

Particularly, the present mixtures according to the invention preferably comprise or consist of component a) in an amount of from 2 wt.-% to 20 wt.-%, preferably of from 2 wt.-% to 10 wt.-%, particularly preferably of from 5 wt.-% to 10 wt.-%, especially preferably of from 5 wt.-% to 8 wt.-% and component b) in an amount of from 98 wt.-% to 80 wt.-%, related to the total mixture, provided that both components a) and b) add up to 100 wt.-%.

This composition according to the invention is particularly advantageous as thus the amount of BDDPA in the final formulation can be regulated such that the final product contains BDDPA in an amount of from approximately 5 ppm to 50 ppm, preferably 10 ppm to 30 ppm, particularly preferably 10 ppm to 20 ppm.

Preferred mixtures according to the invention preferably are of the following composition or consist of:
5-10 wt.-% BDDPA in 95-90 wt.-% Benzyl alcohol, particularly preferably 8-10 wt.-% BDDPA in 92-90 wt.-% Benzyl alcohol, or
1-4 wt.-% BDDPA in 99-96 wt.-% triethyl citrate, or
1-3 wt.-% BDDPA in 99-97 wt.-% triacetin, or
3-6 wt.-% BDDPA in 97-94 wt.-% diethyl succinate, or
5-15 wt.-% BDDPA in 95-85 wt.-% 2-phenyl ethanol, or
5-10 wt.-% BDDPA in 95-90 wt.-% benzyl benzoate, or
1-3 wt.-% BDDPA in 99-97 wt.-% optamint, or
1-4 wt.-% BDDPA in 99-96 wt.-% of further cooling substances as described above, or
2-4 wt.-% BDDPA in 98-96 wt.-% propylene glycol, or 0.5-2 wt.-% BDDPA in 95.5-98 wt.-% ethanol, or
0.5-2 wt.-% BDDPA in 95.5-98 wt.-% menthyl acetate, or
1-4 wt.-% BDDPA in 99-96 wt.-% peppermint oil, or
2-5 wt.-% BDDPA in 98-95 wt.-% anethol,
wherein in each, both components (BDDPA and solvent) in he mixture add up to 100 wt.-%. Particularly preferably, a mixture according to the invention consists of 5-10 wt.-% BDDPA in 95-90 wt.-% benzyl alcohol, particularly preferably 8-10 wt.-% BDDPA in 92-90 wt.-% benzyl alcohol.

Preferred mixtures according to the invention, in which the solvent b) is a binary system, preferably are of the following composition or consist of:
- 5-15 wt.-% BDDPA in 5-10 wt.-% benzyl alcohol and 80-90 wt.-% 2-phenyl ethanol, or
- 5-14 wt.-% BDDPA in 8-12 wt.-% diethyl succinate and 78-87 wt.-% 2-phenyl ethanol, or
- 3-14 wt.-% BDDPA in 38-42 wt.-% triacetin and 48-59 wt.-% benzyl benzoate, or
- 3-5 wt.-% BDDPA in 47-55 wt.-% triethyl citrate and 50-60 wt.-% triacetin, or
- 5-14 wt.-% BDDPA in 80-85 wt.-% 2-phenyl ethanol and 15-20 wt.-% peppermint oil, or
- 5-14 wt.-% BDDPA in 80-85 wt.-% 2-phenyl ethanol and 15-20 wt.-% optamint, or
- 5-7 wt.-% BDDPA in 55-65 wt.-% anethol and 40-45 wt.-% triacetin, or
- 5-8 wt.-% BDDPA in 85-95 wt.-% peppermint oil and 10-12 wt.-% of further cooling substances as described above, or
- 5-14 wt.-% BDDPA in 90-95 wt.-% benzyl alcohol and 5-7 wt.-% of a further cooling substance as described above, wherein in each, both components (BDDPA and solvent) in the mixture always add up to 100 wt.-%.

In a further preferred embodiment, the solvent consists of a combination of more than 4 solvents selected from the group consisting of benzyl alcohol, 2-phenyl ethanol, benzyl benzoate, diethyl succinate, triethyl citrate, triacetin, ethanol, peppermint oil, anethol, optamint, propylene glycol and further cooling substances as described above. Preferably, such a solvent system comprises or consists of five, six, seven, eight, nine, ten or eleven of the previous substances as solvent or, respectively, solvent system for BDDPA.

The mixtures according to the invention, comprising or consisting of a) (E)-3-benzo[1,3]dioxol-5-yl-N,N-diphenyl-2-propenamide and b) at least one solvent selected from the group consisting of benzyl alcohol, 2-phenyl ethanol, benzyl benzoate, diethyl succinate, triethyl citrate, triacetin, ethanol, peppermint oil, anethol, optamint, propylene glycol and further cooling substances as described above, are preferably stable up to 100° C., wherein BDDPA is present in the mixture in a dissolved condition It was found to be advantageous to provide solvents or, respectively, solvent systems in which BDDPA is dissolved and which are stable up to 100° C., preferably up to 90° C., as these mixtures are preferably produced as semi-finished products and have to be further processed. As, in a further processing to the final product, the mixtures have to be heated up to 100° C., preferably up to 90° C. (due to the underlying process), it is advantageous to provide mixtures in which BDDPA is present in a stably dissolved condition up to a temperature of approximately 100° C., preferably up to approximately 90° C.

Particularly, in the mixtures according to the invention, (E)-3-benzo[1,3]dioxol-5-yl-N,N-diphenyl-2-propenamide is preferably present in a dissolved condition in the solvent or, respectively, solvent system already at a room temperature of 23° C. BDDPA is a solid. For a further processing, BDDPA is required to be in dissolved form. Thus it is of (economic) advantage that for dissolving BDDPA or bringing BDDPA into solution possibly low energy is used. Further, the mixture remaining liquid at a room temperature of 23° C. and not crystalizing or becoming likewise unstable such that for dissolving BDDPA the mixture would be needed to be heated, facilitates the storage of liquid BDDPA.

A further important aspect of the present invention are particles, obtainable by subjecting the mixture according to the invention to a spray drying process or spray granuling process.

As the present invention is a semi-finished product, which is further processed by addition to final products, it was found to be advantageous to further process the mixture according to the invention by spray drying or spray granuling it, particularly with regard to the easier handling, storage and compactness of the mixture.

A further aspect of the present invention are thus also semi-finished products, comprising or substantially consisting of mixtures according to the invention or (spray dried or, respectively, spray granule) particles thereof.

A further aspect of the present invention relates to cosmetic and/or dermatologic compositions comprising the mixtures described above or, preferably, in an amount of approximately 0.1 to approximately 10 wt.-%, particularly approximately 0.5 to approximately 8 wt.-% and especially approximately 1 to approximately 5 wt.-%. These compositions can be skin compositions, body care compositions or hair treatment compositions including sunblockers and oral and dental care compositions as well as (medical) chewing gums. Particularly preferred applications in the field of cosmetic or dermatologic compositions are shower baths, shampoos, soaps, air refresheners and the like.

The particularly preferred pharmaceutical compositions include substances for relieving pain of mucous membranes, particularly syrups, sprays, lozenges and candies against a cold.

Preferably, the present invention comprises or consists of products containing the mixtures or particles according to the invention, wherein the products are selected from the group consisting of foodstuffs, oral care compositions, body care compositions or pharmaceutical compositions.

The cosmetic, dermatologic and/or pharmaceutical compositions according to the invention can contain further adjuvants or additives, such as for example surfactants, oil bodies, emulsifiers, pearlescent waxes, consistency enhancers, thickeners, superfattening agents, stabilizers, polymers, silicone compounds, fats, wyes, leithins, phospholipids, UV blockers, humectants, biogenic active substances, antioxidants, anti-deodorants, transpirants, antidandruff agents, film formers, swelling agents, insect repellants, tanning agents, tyrosin inhibitors (depigmentation agent), hydrotopes, solubilisers, preservatives, perfume oils, dyes and the like.

INDUSTRIAL APPLICABILITY

A further aspect of the invention relates to the use of at least one solvent selected from the group consisting of or substantially consisting of benzyl alcohol, 2-phenyl ethanol, benzyl benzoate, diethyl succinate, triethyl citrate, triacetin, ethanol, peppermint oil, anethol, optamint, propylene glycol and further cooling substances as described above or mixtures thereof for dissolving solid (E)-3-benzo[1,3]dioxol-5-yl-N,N-diphenyl-2-propenamide, wherein preferably (E)-3-benzo[1,3]dioxol-5-yl-N,N-diphenyl-2-propenamide is present as dissolved in said solvent or, respectively, mixtures thereof at room temperature (23° C.).

The preferred solvents as described above, particularly benzyl alcohol, but also the preferred binary, ternary and quarternary solvent systems are preferably applied for the described use according to the invention.

A further aspect of the present invention further relates to a solvent system for dissolving (E)-3-benzo[1,3]dioxol-5-yl-N,N-diphenyl-2-propenamide, selected from the group or substantially consisting of at least one compound or at least two, three, four, five, six, seven, eight, nine, ten or all compounds of from the group consisting of benzyl alcohol, 2-phenyl ethanol, benzyl benzoate, diethyl succinate, triethyl citrate, triacetin, ethanol, peppermint oil, anethol, optamint, propylene glycol and further cooling substances as described above, wherein preferably (E)-3-benzo[1,3]dioxol-5-yl-N,N-diphenyl-2-propenamide is present as dissolved in said solvent or, respectively, mixtures thereof at room temperature (23° C.).

Particularly preferably, the solvent systems for dissolving (E)-3-benzo[1,3]dioxol-5-yl-N,N-diphenyl-2-propenamide comprise or consist of the previously described preferred embodiments of solvents, particularly benzyl alcohol, but also the preferred binary, ternary and quarternary solvent systems.

Particularly preferred is a mixture according to the invention, comprising or substantially consisting of a) (E)-3-benzo[1,3]dioxol-5-yl-N,N-diphenyl-2-propenamide and b) at least one substance selected from the group consisting of benzyl alcohol, 2-phenyl ethanol, benzyl benzoate, diethyl succinate, triethyl citrate, triacetin, ethanol, peppermint oil, anethol, optamint, propylene glycol and further cooling substances as described above or mixtures thereof. The preferred combinations as described above can also be applied here for the combination of substance a) with substances b), particularly with benzyl alcohol but also particularly the preferred binary, ternary and quarternary solvent systems.

Particularly preferred is a mixture according to the invention comprising or substantially consisting of 8-10 wt.-% BDDPA in 92-90 wt.-% benzyl alcohol.

EXAMPLES

Example 1

Solubility of (E)-3-benzo[1,3]dioxol-5-yl-N,N-diphenyl-2-propenamide

The solubility of (E)-3-benzo[1,3]dioxol-5-yl-N,N-diphenyl-2-propenamide (BDDPA) in different solvents was tested. It was found that the formulations in table 1 were stable at room temperature (23° C.).

TABLE 1

Stable at room temperature (23° C.), solved formulations of BDDPA (amounts as wt.-%)

| Mixture | Solvent | BDDPA |
|---|---|---|
| 1 | Ethanol, | 1 |
| 2 | Menthyl acetate, | 1 |
| 3 | Benzyl alcohol | 10 |
| 4 | Triethyl citrate, | 3 |
| 5 | Triethyl citrate | 2 |
| 6 | Triethyl citrate | 1 |
| 7 | Triacetin | 3 |

TABLE 1-continued

Stable at room temperature (23° C.), solved formulations of BDDPA (amounts as wt.-%)

| Mixture | Solvent | BDDPA |
|---|---|---|
| 8 | Triacetin | 2 |
| 9 | Peppermint oil | 3 |
| 10 | Peppermint oil | 2 |
| 11 | Optamint | 3 |
| 12 | Optamint | 2 |
| 13 | Peppermint oil | 3 |
| 14 | Peppermint oil | 2 |
| 15 | Frescolat ®MPC | 2 |
| 16 | Frescolat ®MPC | 1 |
| 17 | Anethol | 5 |
| 18 | Anethol | 3 |

The amount of solvent added to the amount of (E)-3-benzo[1,3]dioxol-5-yl-N,N-diphenyl-2-propenamide is added up to 100 wt.-% in each mixture (1 to 18). Thus the composition of mixture 1 is 99 wt.-% ethanol, 1 wt.-% BDDPA.

The table shows that BDDPA dissolves in the present solvents already at temperatures ≤65° C., where necessary by means of ultrasonification, and that BDDPA is completely dissolved in the respective solvents at room temperature (23° C.).

Example 2

Stability at 5° C.

Several of the mixtures of example 1 were stored at night at 5 C to observe the stability. It was found that the formulations in table 2 are present in stable form.

TABLE 2

Stability of the formulation after storage of 12 h at 5° C. (amounts as wt.-%)

| Mixture | Solvent | BDDPA |
|---|---|---|
| 1 | Ethanol | 1 |
| 2 | Menthyl acetate | 1 |
| 3 | Benzyl alcohol | 10 |
| 5 | Triethyl citrate | 2 |
| 6 | Triethyl citrate | 1 |
| 8 | Triacetin | 2 |
| 10 | Peppermint oil | 2 |
| 12 | Optamint | 2 |
| 16 | Frescolat ® MPC | 1 |
| 18 | Anethol | 3 |

The amount of solvent added to the amount of (E)-3-benzo[1,3]dioxol-5-yl-N,N-diphenyl-2-propenamide is added up to 100 wt.-% in each mixture (1 to 18). Thus the composition of mixture 1 is 99 wt.-% ethanol, 1 wt.-% BDDPA.

The table shows that BDDPA remains stably dissolved in the solvent over night, even when the room temperature is below room temperature, no recrystallization occurs.

Example 3

Solubility of BDDPA in Binary and Ternary Solvent Systems

The solubility of (E)-3-benzo[1,3]dioxol-5-yl-N,N-diphenyl-2-propenamide (BDDPA) in different solvent combinations was tested. Table 3 shows a summary of the tested formulations.

TABLE 3

Solubility of BDDPA in solvent combinations at 23° C. and 90° C. (amounts as wt.-%)

| Mixture | BDDPA | Solvent 1 | Solvent 2 | Solvent 3 |
|---|---|---|---|---|
| 19 | 5 | Triacetin 47.5 | Peppermint oil 47.5 | — |
| 20 | 5 | Triethyl citrate 47.5 | Peppermint oil 47.5 | — |
| 21 | 5 | Triethyl citrate 95.0 | — | — |
| 22 | 5, 2 | Triethyl citrate 31.6 | Triacetin 31.6 | Peppermint oil 31.6 |
| 23 | 5 | Triacetin 45.0 | Triethyl citrate 50.0 | — |
| 24 | 5 | Triacetin 25.0 | Triethyl citrate 50.0 | Peppermint oil 20.0 |

The amount of solvents 1 to 3 add up to 100 wt.-% with the amount of (E)-3-benzo[1,3]dioxol-5-yl-N,N-diphenyl-2-propenamide. Thus the composition of mixture 19 is 5 wt.-% BDDPA, 47.5 wt.-% triacetin and 47.5 wt.-% peppermint oil.

It was found that BDDPA is completely dissolved in binary and ternary solvent combinations at room temperature (23° C.) and also remains stably dissolved at high temperatures of 90° C.

Example 4

Solubility of BDDPA at High Temperatures

The behaviour of (E)-3-benzo[1,3]dioxol-5-yl-N,N-diphenyl-2-propenamide (BDDPA) with regard to its solubility was tested in different solvent combinations at high temperatures. Table 4 shows the composition of the tested mixtures. The results are summed up in table 5.

TABLE 4

Composition of the tested mixtures 25-31

| Solvent | 25 | 26 | 27 | 28 | 29 | 30 | 31 |
|---|---|---|---|---|---|---|---|
|  | wt.-% | | | | | | |
| BDDPA | 10 | 10 | 10 | 15 | 10 | 10 | 10 |
| Triacetin | — | — | — | — | — | — | 40 |
| Triethyl citrate | — | 32 | — | — | — | — | — |
| Benzyl alcohol | — | 8 | 8 | — | — | — | — |
| Diethyl succinate | — | 50 | — | — | 10 | — | — |
| 2-Phenyl ethanol | 90 | — | 82 | 85 | 80 | — | — |
| Benzyl benzoate | — | — | — | — | — | 90 | 50 |

TABLE 5

Results of the solubility of BDDPA at high temperatures

| | Solubility | | | |
|---|---|---|---|---|
| Mixture | 60° C. | 70° C. | 80° C. | Recrystallisation |
| 25 | Partially | Partially | Completely | No |
| 26 | Partially | Partially | Completely | <40° C. |
| 27 | Partially | Partially | Completely | No |
| 28 | Partially | Partially | Completely | No |
| 29 | Partially | Partially | Completely | No |
| 30 | Completely | Completely | Completely | No (yes, after 2 days) |
| 31 | Completely | Completely | Completely | No (yes, after 2 days) |

Tables 3, 4 and 5 show exemplary mixtures which may be preferably used for a further processing (e.g. spray drying), as in this case, the mixture for dissolving is warmed up to 90° C. for at most 30 minutes and then cooled down to 50-60° C. for further processing and can be stably stored at this temperature without precipitation (up to 6 hours).

APPLICATION EXAMPLES a) Oral Care

Application Example FM-1: Mouthwash

Suitable mouthwashes can be produced according to the following base recipe:

| Amount (wt.-%) | Type of ingredient | Examples of ingredients |
|---|---|---|
| 0.01-0.1 | Antibacterial agent | Beta-naphthol, thymol, chlorthymol and hexylresorcin |
| 5-25 | Humectant | Glycerine, sorbit, Propylene glycol and polyalkylene glycol |
| 0.01-0.2 | Essential oil | Carnation oil, peppermint oil and spearmint oil |
| 0-30 | Ethanol | |
| 0-5 | Polymer | Polyoxyalkyleneblock copolymers Mw 5000-30000 |
| 40-80% | Water | |
| 0.0125-55 | Mixture according to the invention | see Table1 and Table 3 |
| 0-10 | Further ingredients | |

A mouthwash of the following composition is produced:

| Amount | | Ingredient |
|---|---|---|
| 220.75 | mL | Ethanol 95% |
| 250 | g | Sorbit 70% |
| 6.25 | mL | 8 wt.-% BDDPA in 92 wt.-% benzyl alcohol |
| 0.30 | g | Peppermint oil, |
| 0.64 | g | Methyl salicylate |
| 0.922 | g | Eucalyptol |
| 0.639 | g | Thymol |
| 1.50 | g | Benzoic acid |
| 5.00 | g | Pluronic ® F127 Non-ionic surfactant |
| 0.60 | g | Sodium-Saccharin |
| 0.30 | g | Sodium citrate |
| 0.10 | g | Citric acid |
| q.s. 1 | Liter | Water |

For the production of a mouthwash, the components as described above are mixed with each other in the indicated amounts.

Application Example FM-2: Toothpaste

Suitable toothpastes can be produced according to the following base recipe:

| Amount (wt.-%) | Type of ingredient | Examples of ingredients |
|---|---|---|
| 0.05-0.2 | Fluoride | Sodium fluoride, tin(II)-fluoride, sodium monofluoro phosphate; |
| 10-55 | Humectant | Glycerine, Sorbit, Propylene glycol, Polyalkylene glycol |

-continued

| Amount (wt.-%) | Type of ingredient | Examples of ingredients |
|---|---|---|
| 0-50 | Polymer | Polyoxyalkylene blockcopoymers Mw 5000-30000 |
| 10-50 | Water | |
| 10-55 | Abrasives | Calcium pyrophosphate, Dicalcium phosphate, Silicon oxide hydrate; |
| 2-10 | Binders | Karayagum, tragacanth USP, sodium alginate, Irish moss, methyl cellulose |
| 2-8 | Surfactants | Sodium laurylsulphat, Sodium-N-laurylsarcosinate, Dioctylsodium sulphosuccinate, Sodium lauryl sulphoacetate |
| 0-10 | Peroxigen compounds | Hydrogen peroxide, inorganic peroxides |
| 0.0125-55% | Mixture according to the invention | |
| 0-10 see above | Further ingredients | |

Application Example FM-3: Chewing Gum

Suitable chewing gums can be produced according to the following base recipe:

| Amount (wt.-%) | Ingredient |
|---|---|
| 15-25 | gum-base |
| 20-30 | Glucose syrup |
| 50-60 | Powdered sugar |
| 0.1-10 | Mixture according to the invention |
| 1-2 | Plasticizer (e.g. Glycerine) |
| 3-6 | Water |

Instead of the glucose syrup and the powdered sugar, the sugar alcohols mannite, xylite and sorbit, "palatinit" and others as well as artificial sweeteners such as saccharine cyclamate, acesulfam-K and aspartame can be used for "sugar-free" recipes.

b) Body Care

Application Example FM-4: Hair Tonic

| Phase | Amount (wt.-%) | Ingredient (INCI) |
|---|---|---|
| A | q.s. | Perfume oil |
|   | 1.00 | PEG-40 Hydrogenated Castor Oil |
| B | 59.0-65.0 | Alcohol |
|   | 1.0 | Panthenol |
|   | 0.5 | Polyquarternium-16 |
|   | 0.1 | Menthol |
|   | 32 | Aqua dem. |
|   | 0.0625-6.25 | 8 wt.-% BDDPA in 92 wt.-% benzyl alcohol |

Production: Mix phase A. Add phase B and stir until everything is dissolved, adjust pH value to pH 7.0.

Application Example FM-5: Hair Gel

| Phase | Amount (wt.-%) | Ingredient (INCI) |
|---|---|---|
| A | 45.00 | Carbopol 940 1% in water |
|   | 0.70 | Aminomethyl propanol |
| B | 7.50 | VP/Methacrylamide/Vinyl Imidazole Copolymer |
|   | 0.10 | Perfume oil |
|   | 0.30 | PEG-40 Hydrogenated Castor Oil |
|   | 0.30 | Preservative |
|   | 0.05 | Disodium EDTA |
|   | 0.30 | Panthenol |
|   | 6.75-12.94 | Alcohol |
|   | 0.0625-6.25 | 8 wt.-% BDDPA in 92 wt.-% Benzyl alcohol |
|   | 32.75 | Aqua dem. |

Production: Weigh components of phase A and homogenize. Dissolve phase B and add while stirring to phase A. Adjust pH value to pH 6.9.

Application Example FM-6: Cosmetic Sun Blocker Composition

A cosmetic sun blocker composition comprising a combination of at least inorganic pigment and organic UV-filters is described in the following recipes.

The production of the subsequently listed formulations is accomplished by typical manner known to the person skilled in the art.

| Phase | Amount (wt.-%) | Component | Ingredient (INCI) |
|---|---|---|---|
| A | 7.50 | Uvinul MC80 | Ethylhexyl cinnamate |
|   | 2.00 | Uvinul M 40 | Benzophenon-3 |
|   | 0.80 | Rylo PG 11 | Polyglyceryldimersoyate |
|   | 1.00 | Span 60 | Sorbitan stearate |
|   | 0.50 | Vitamin E-Acetate | Tocopheryl acetate |
|   | 3.00 | Dracorin 100 SE | Glyceryl stearate, PEG-100 Stearate |
|   | 1.00 | Cremophor CO 410 | PEG-40-hydrated castor oil |
| B | 3.00 | T-Lite SF | Titanium dioxide, Aluminium oxide hydrate, Dimethicon-/Methicon Copolymer |
|   | 1.00 | Cetiol SB 45 | *Butyrospermum parkii* (Shea Butter) |
|   | 6.50 | Finsolv TN | C12-15-Alkyl benzoate |
| C | 5.00 | Butylen glycol | Butylene glycol |
|   | 0.30 | Keltrol | Xanthangum |
|   | 0.10 | Edeta BD | Disodium -EDTA |
|   | 0.10 | Allantoin | Allantoin |
|   | Ad 100 | Water dem. | Aqua dem. |
| D | 1.00 | Sepigel 305 | Polyacrylamide, C13-14-Isoparaffine, Laureth-7 |
|   | 0.0125-12.5 | 0.0125-12.5% | Mixture according to the invention |
|   | q.s. |   | Preservative |

Application Example FM-7: Moisturizing Body Lotion

| Phase | Amount (wt.-%) | Ingredient (INCI) |
|---|---|---|
| A | 6.0 | PEG-7-hydrated castor oil |
|   | 10.0 | Cetearyl ethyl hexanoate |
|   | 5.0 | Isopropyl myristate |
|   | 7.0 | Mineral oil |
|   | 0.5 | Shea Butter (*Butyrospermum parkii*) |

-continued

| Phase | Amount (wt.-%) | Ingredient (INCI) |
|---|---|---|
|  | 0.5 | Aluminum stearate |
|  | 0.5 | Magnesium stearate |
|  | 0.2 | Bisabolol |
|  | 0.7 | Quaternium-18-Hectorite |
| B | 5.0 | Dipropylene glycol |
|  | 0.7 | Magnesium sulfate |
|  | q.s. | Preservative |
|  | 50-62.9 | Aqua dem. |
|  | q.s. | Perfume oil |
| C | 0.0125-12.5 | 8 wt.-% BDDPA in 92 wt.-% Benzyl alcohol |

Production: Warm the phases A and B separated from each other to approximately 80° C. Stir phase B into phase A and homogenize. Cool down to approximately 40° C. while stirring, add phase C and homogenize again. Cool down to room temperature while stirring.

Application Example FM-8: Caring Shampoo

| Phase | Amount (wt.-%) | Ingredient (INCI) |
|---|---|---|
| A | 30.0 | Sodium laurethsulfate |
|  | 6.0 | Sodium ocoamphoacetate |
|  | 6.0 | Cocamidopropyl betaine |
|  | 3.0 | Sodium laurethsulfate, Glycol distearate, Cocamid-MEA, Laureth-10 |
|  | 0.0125-12.5 | 8 wt.-% BDDPA in 92 wt.-% Benzyl alcohol |
|  | 7.7 | Polyquaternium-44 |
|  | 2.0 | Amodimethicon |
|  | q.s. | Perfume oil |
|  | q.s. | Preservatives |
|  | 1.0 | Sodium chloride |
|  | 30-42 | Aqua dem. |
| B | q.s. | Citric acid |

Production: Mix the components of phase A and dissolve. Adjust the pH value to 6-7 with citric acid.

Application Example FM-9: Shower Gel

| Phase | Amount (wt.-%) | Ingredient (INCI) |
|---|---|---|
| A | 40.0 | Sodium laurethsulfate |
|  | 5.0 | Decylglucoside |
|  | 5.0 | Cocamidopropyl betaine |
|  | 0.0125-12.5 | 8 wt.-% BDDPA in 92 wt.-% Benzyl alcohol |
|  | 1.0 | Panthenol |
|  | q.s. | Perfume oil |
|  | q.s. | Preservatives |
|  | 2.0 | Sodium chloride |
|  | 32-45 | Aqua dem. |
| B | q.s. | Citrit acid |

Production: Mix the components of phase A and dissolve. Adjust the pH value to 6-7 with citric acid.

Application Example FM-10: Shampoo

| Phase | Amount (wt.-%) | Ingredient (INCI) |
|---|---|---|
| A | 40.0 | Sodium laurethsulfate |
|  | 5.0 | Sodium -C12-15-Pareth-15-sulfonate |
|  | 5.0 | Decylglucoside |
|  | q.s. | Perfume oil |

-continued

| Phase | Amount (wt.-%) | Ingredient (INCI) |
|---|---|---|
|  | 0.1 | Phytantriol |
|  | 31-43 | Aqua dem. |
|  | 0.0125-12.5 | 8 wt.-% BDDPA in 92 wt.-% Benzyl alcohol |
|  | 0.3 | Polyquaternium-10 |
|  | 1.0 | Panthenol |
|  | q.s. | Preservatives |
|  | 1.0 | Laureth-3 |
|  | 2.0 | Sodium chloride |

Production: Mix the components of phase A and dissolve. Adjust the pH value to 6-7 with citric acid.

Application Example FM-11: Foot Balm

| Phase | Amount (wt.-%) | Ingredient (INCI) |
|---|---|---|
| A | 2.0 | Ceteareth-6, Stearyl alcohol |
|  | 2.0 | Ceteareth-25 |
|  | 5.0 | Cetearylethyl hexanoate |
|  | 4.0 | Cetyl alcohol |
|  | 4.0 | Glyceryl stearate |
|  | 5.0 | Mineral oil |
|  | 0.2 | Menthol |
|  | 0.5 | Camphor |
| B | 57.8-69 | Aqua dem. |
|  | q.s. | Preservatives |
| C | 1.0 | Bisabolol |
|  | 1.0 | Tocopheryl acetate |
| D | 0.0125-12.5 | 8 wt.-% BDDPA in 92 wt.-% Benzyl alcohol |
|  | 5.0 | Witch hazel extract |

Production: Heat the components of phases A and B separated from each other to 80° C. Stir phase B into phase A while homogenizing. Cool down to approximately 40° C. while stirring, add phases C and D and quickly homogenize again. Cool down to room temperature while stirring.

Application Example FM-12: Facial Cleansing Lotion—Type O/W

| Phase | Amount (wt.-%) | Ingredient (INCI) |
|---|---|---|
| A | 10.0 | Cetearylethyl hexanoate |
|  | 10.0 | Capryl-/Caprin triglyceride |
|  | 1.5 | Cyclopentasiloxane, Cyclohexasilosane |
|  | 2.0 | PEG-40-hydrated castor oil |
| B | 3.5 | Capryl-/Caprintriglyceride, Sodium acrylate-copolymer |
| C | 1.0 | Tocopheryl acetate |
|  | 0.2 | Bisabolol |
|  | q.s. | Preservatives |
|  | q.s. | Perfume oil |
| D | 3.0 | Polyquaternium-44 |
|  | 0.5 | Cocotrimoniummethosulfate |
|  | 0.5 | Ceteareth-25 |
|  | 2.0 | Panthenol, Propylene glycol |
|  | 4.0 | Propylene glycol |
|  | 0.1 | Disodium -EDTA |
|  | 0.0125-12.5 | 8 wt.-% BDDPA in 92 wt.-% Benzyl alcohol |
|  | 49-59.7 | Aqua dem. |

Production: Dissolve phase A, stir phase B into phase A, add phase C to the combined phases A and B. Dissolve phase D, add to the combined phases A, B and C and homogenize. Stir for 15 minutes.

Application Example FM-13: Body-Spray

| Phase | Amount (wt.-%) | Ingredient (INCI) |
|---|---|---|
| A | 3.0 | Ethylhexylmethoxy cinnamate |
|  | 2.0 | Diethylaminohydroxybenzoylhexyl benzoate |
|  | 1.0 | Polyquaternium-44 |
|  | 3.0 | Propylene glycol |
|  | 2.0 | Panthenol, Propylene glycol |
|  | 1.0 | Cyclopentasiloxan, Cyclohexasilosan |
|  | 10.0 | Octyldodecanol |
|  | 0.5 | PVP |
|  | 10.0 | Capryl-/Caprin triglyceride |
|  | q.s. | Perfume oil |
|  | 3.0 | C12-15-Alkyl benzoate |
|  | 3.0 | Glycerine |
|  | 1.0 | Tocopheryl acetate |
|  | 0.3 | Bisabolol |
|  | 0.0125-12.5 | 8 wt.-% BDDPA in 92 wt.-% Benzyl alcohol |
|  | 46.7-58 | Alcohol |

Production: Weigh the components of phase A and dissolve to a clear solution.

Application Example FM-14: Skin Care Gel

| Phase | Amount (wt.-%) | Ingredient (INCI) |
|---|---|---|
| A | 3.6 | PEG-40-hydrated castor oil |
|  | 15.0 | Alcohol |
|  | 0.1 | Bisabolol |
|  | 0.5 | Tocopheryl acetate |
|  | q.s. | Perfume oil |
| B | 3.0 | Panthenol |
|  | 0.6 | Carbomer |
|  | 0.0125-12.5 | 8 wt.-% BDDPA in 92 wt.-% Benzyl alcohol |
|  | 62.9-75.4 | Aqua dem. |
| C | 0.8 | Triethanol amine |

Application Example FM-15: After-Shave-Lotion

| Phase | Amount (wt.-%) | Ingredient (INCI) |
|---|---|---|
| A | 10.0 | Cetearylethyl hexanoate |
|  | 5.0 | Tocopheryl acetate |
|  | 1.0 | Bisabolol |
|  | q.s. | Perfume oil |
|  | 0.3 | Acrylate/C10-30 Alkylacrylate-Crosspolymer |
| B | 15.0 | Alcohol |
|  | 1.0 | Panthenol |
|  | 3.0 | Glycerine |
|  | 0.125-12.5 | 8 wt.-% BDDPA in 92 wt.-% Benzyl alcohol |
|  | 0.1 | Triethanolamine |
|  | 51.1-63.6 | Aqua dem. |

Production: Mix the components of phase A. Dissolve phase B, add to phase A and homogenize.

Application Example FM-16: After-Sun-Lotion

| Phase | Amount (wt.-%) | Ingredient (INCI) |
|---|---|---|
| A | 0.4 | Acrylate/C10-30-Alkylacrylate-Crosspolymer |
|  | 15.0 | Cetearylethyl hexanoate |
|  | 0.2 | Bisabolol |
|  | 1.0 | Tocopheryl acetate |
|  | q.s. | Perfume oil |
| B | 1.0 | Panthenol |
|  | 15.0 | Alcohol |
|  | 3.0 | Glycerine |
|  | 0.0125-12.5 | 8 wt.-% BDDPA in 92 wt.-% Benzyl alcohol |
|  | 50-63.2 | Aqua dem. |
| C | 0.2 | Triethanolamine |

Production: Mix the components of phase A. Add phase by while homogenising. Neutralize with phase C and homogenize again.

Application Example FM-17: Sun Blocker Lotion

| Phase | Amount (wt.-%) | Ingredient (INCI) |
|---|---|---|
| A | 4.5 | Ethylhexylmethoxy cinnamate |
|  | 2.0 | Diethylaminohydroxybenzoylhexyl benzoate |
|  | 3.0 | Octocrylene |
|  | 2.5 | Di-C12-13-Alkylmalate |
|  | q.s. | Perfume oil |
|  | 0.5 | Tocopheryl acetate |
|  | 4.0 | Polyglyceryl-3-methylglucose distearate |
| B | 3.5 | Cetearyl isononanoate |
|  | 1.0 | VP-/EicosenCopolymer |
|  | 5.0 | Isohexadecane |
|  | 2.5 | Di-C12-13-Alkylmalate |
|  | 3.0 | Titanium dioxide, Trimethoxycaprylylsilane |
| C | 5.0 | Glycerine |
|  | 1.0 | Sodium cetearylsulfate |
|  | 0.5 | Xanthangum |
|  | 47.2-59.7 | Aqua dem. |
| D | 0.0125-12.5 | 8 wt.-% BDDPA in 92 wt.-% Benzyl alcohol |
|  | 1.0 | Phenoxy ethanol, Methyl paraben, Ethyl paraben, Butyl paraben, Propyl paraben, Isobutyl paraben |
|  | 0.3 | Bisabolol |

Production: Heat the components of phases A and B separated from each other to approximately 80° C. Add phase B into phase A while stirring and homogenize. Heat up phase C to approximately 80° C. and add while stirring and homogenizing into the combined phases A and B. Cool down to approximately 40° C. while stirring, add phase D and homogenize again.

Application Example FM-18: Patch

50 Parts of active substance according to production example H 3-7 were dispersed in 100 parts of a 10% sodium lauryl sulfate solution during strong stirring and heating to 50° C. 880 parts of a 50% butylacrylate dispersion were stirred into the obtained emulsion and the obtained polymer-dispersion containing active substance was spread out with a suitable spreading scraper on a polyester foil with a thickness of 15 μm (Fa. Kalle, D-Wiesbaden) and was dried at 35 to 40° C. at controlled humidity. Depending on the settings of the scraper, surface weights of 5 mg/cm$^2$ were obtained, which could be further increased by multiple spreading. The self-sealing film produced thereby and with an amount of active substance of 5% was furnished with a siliconized release sheet made of polyester (Scotch Pak 75 mu m, 3M) and was cut into the desired dimensions.

The amounts each relate parts by weight.

c) Foodstuff

Application Example FM-19: Pudding

Recipe (for 100 ml)

| Ingredient | Amount |
| --- | --- |
| Fat-free dry milk | 10.715 g |
| Saccharose | 5 g |
| Novelose Starch, National Starch | 7 g |
| Mixture of vegetable oils | 2.2 g |
| Carrageenan | 0.016 g |
| Vanilla aroma | 0.5 g |
| Sodium stearoyl-2-lactylate | 0.095 g |
| Yellow dye | 0.189 g |
| Magnesium phosphate | 0.165 g |
| Vitamin pre-mixture | 1.84 g |
| Trace element pre-mixture | 0.015 g |
| 8 wt.-% BDDPA in 92 wt.-% Benzyl alcohol | 30 mg |
| Water | 76.19 g |

Production: Heat nine tenths of water to 43.3° C. Dissolve the fat-free dry milk in the water. Heat the oil to 60° C. and add carrageenan and oil soluble vitamins to the oil. Add oil into the product. Add the further components except for the modified starch, vanilla aroma and the vitamin pre-mixture. Homogenise the mixture. Slowly add starch. Add active substance, vitamins and aroma. Standardise the solids content. Heat in sterile units and pack into cans.

d) Application Example FM-20: Textile Equipment with Mixture According to the Invention First, an aqueous slurry of amylose-containing starch is produced by adding 10 g of a customary preservative into 570 g deionized water. 20 g carboxymethyl cellulose were dissolved herein, subsequently 400 g of amylose-containing starch with an amylose content of 50 wt.-% were added and a slurry was produced while stirring.

Subsequently, the production of aqueous solutions for treating textile containing amylose-containing starch was produced according to one of the two following methods:

Method 1: The respective slurry is adjusted to a starch-amount of 5 or 15 wt.-% by dilution with water.

Method 2: The respective slurry is first diluted to a starch-amount of 5 or 15 wt.-% by dilution with water and subsequently 30 g/l of a 30 wt.-% aqueous polyurethane dispersion (non-ionogenic) is added.

Subsequently, the equipment of a tissue with amylose-containing starch and a mixture according to the invention is performed.

A cotton tissue sample with a surface weight of 124 g/m² is treated with the aqueous solution produced above by means of a foulard up to an absorption of 80 wt.-% of aqueous solution, related to the weight of the tissue. Subsequently it is dried for 2 min at 120° C.

Subsequently the tissue samples equipped in this manner are treated with an aqueous formulation mixture according to the invention by foularding an aqueous emulsion/suspension of a mixture according to the invention with an amount of BDDPA of 1 to 7 wt.-% up to an absorption of 79-80 wt.-% on the tissue sample. Subsequently, the tissue samples treated such are dried in a household dryer up to a remaining humidity of 15%.

The tissues loaded with active substance and produced in such a way can further be examined as e.g. on their cooling effect when contacted with skin or their repelling effect on insects.

e) Aroma Composition

All indications, if not stated otherwise, are in wt.-%.

Aroma Composition FM-21:

Production of aromas with a cooling effect of the eucalyptus-menthol-type by using the mixture according to the invention:

A solution A with the following composition was mixed with different mixtures according to the invention such that aroma compositions a-h were obtained.

Solution A:

| Component | Amount (wt.-%) |
| --- | --- |
| Anethol | 10 |
| Peppermint oil *Mentha piperita* type Willamette | 20 |
| Peppermint oil *Mentha arvensis*, rectified | 20 |
| I-Menthyl lactate | 1 |
| 2-Hydroxyethylmenthyl carbonate | 2 |
| 2-Hydroxypropyl-menthyl carbonate | 2 |
| 1,8-Cineol (Eucalyptol) | 5 |
| I-Menthol | 40 |
| Total | 100 |

|  | Aroma composition | | | | | | | |
| --- | --- | --- | --- | --- | --- | --- | --- | --- |
|  | a | b | c | d | e | f | g | h |
|  | Amount (wt.-%) | | | | | | | |
| 8 wt.-% BDDPA in 92 wt.-% Benzyl alcohol | 6.25 | | | | | | | |
| 2 wt.-% BDDPA in 98 wt.-% Frescolat MPC | | 25 | | | | | | |
| 5 wt.-% BDDPA in 95 wt.-% Anethol | | | 4 | | | | | |
| 5 wt.-% BDDPA in 47.5 wt.-% Triethyl citrate + 47.5 wt.-% Peppermint oil | | | | 10 | 10 | | | |
| 5.2 wt.-% BDDPA in 31.6 wt.-% Triethyl citrate + 31.6 wt.-% Triacetin + 31.6 wt.-% Peppermint oil | | | | | | 10 | | |

-continued

|  | Aroma composition | | | | | | | |
|---|---|---|---|---|---|---|---|---|
|  | a | b | c | d | e | f | g | h |
|  | Amount (wt.-%) | | | | | | | |
| 5 wt.-% BDDPA in 47.5 wt.-% Triacetin + 47.5 wt.-% Frescolat ® ML |  |  |  |  |  | 10 |  |  |
| 3 wt.-% BDDPA in 47 wt.-% 2-Phenyl ethanol + 50 wt.-% Frescolat ® MPC |  |  |  |  |  |  | 16.6 |  |
| 10 wt.-% BDDPA in 90 wt.-% Benzyl alcohol |  |  |  |  |  | 5 |  | 5 |
| Solution A | 93.75 | 75 | 86 | 90 | 90 | 85 | 83.4 | 95 |
| Total | 100 | 100 | 100 | 100 | 100 | 100 | 100 | 100 |

The aromas obtained in such manner were added to a standard toothpaste mass based on silica in a concentration of 1.2 wt.-%.

Aroma Composition FM-22:

Production of aromas with a cooling effect of the spearmint-type by using the cooling substances according to the invention.

A solution A with the following composition was mixed with different mixtures according to the invention such that aroma compositions a-h were obtained.

Solution A:

| Component | Amount (wt.-%) |
|---|---|
| Menthol | 30 |
| Carvon | 20 |
| Spearmint oil type native | 20 |
| Anethol | 5 |
| Peppermint oil *mentha arvensis* rectified | 10 |
| Peppermint oil *Mentha piperita* type Willamette | 15 |
| Total | 100 |

The obtained aromas were added to a toothpaste mass in a concentration of 1.2%, which consists to an amount of 65% of sodium bicarbonate.

Aroma composition FM-23: Production of aromas with a cooling effect and a spicy-aromatic taste impression type by using the cooling substances according to the invention.

A solution A with the following composition was mixed with different mixtures according to the invention such that aroma compositions a-h were obtained.

Solution A:

| Component | Amount (wt.-%) |
|---|---|
| l-Menthol | 30 |
| Peppermint oil *Mentha arvensis*, rectified | 25 |
| Peppermint oil *Mentha piperita* type Willamette | 15 |
| Anethol | 10 |
| Spearmint oil type native | 10 |
| Cinnamon aldehyde | 5 |
| Eugenol | 5 |
| Total | 100 |

|  | Aroma composition (wt.-%) | | | | | | | |
|---|---|---|---|---|---|---|---|---|
|  | a | b | c | d | e | f | g | h |
| 8 wt.-% BDDPA in 92 wt.-% Benzyl alcohol | 9.4 |  |  |  |  |  |  |  |
| 2 wt.-% BDDPA in 98 wt.-% Frescolat MPC |  | 37.5 |  |  |  |  |  |  |
| 5 wt.-% BDDPA in 95 wt.-% Anethol |  |  | 15 |  |  |  |  |  |
| 5 wt.-% BDDPA in 47.5 wt.-% Triethyl citrate + 47.5 wt.-% Peppermint oil |  |  | 15 | 15 |  |  |  |  |
| 5.2 wt.-% BDDPA in 31.6 wt.-% Triethyl citrate + 31.6 wt.-% Triacetin + 31.6 wt.-% Peppermint oil |  |  |  | 15 |  |  |  |  |
| 5 wt.-% BDDPA in 47.5 wt.-% Triacetin + 47.5 wt.-% Frescolat ® ML |  |  |  |  | 15 |  |  |  |
| 3 wt.-% BDDPA in 47 wt.-% 2-Phenyl ethanol + 50 wt.-% Frescolat ® MPC |  |  |  |  |  | 25 |  |  |
| 10 wt.-% BDDPA in 90 wt.-% Benzyl alcohol |  |  |  |  |  | 7.5 |  | 7.5 |
| Solution A | 92.5 | 66.5 | 70 | 85 | 85 | 77.5 | 75 | 92.5 |
| Total | 100 | 100 | 100 | 100 | 100 | 100 | 100 | 100 |

| | Aroma composition | | | | | | | |
|---|---|---|---|---|---|---|---|---|
| | a | b | c | d | e | f | g | h |
| | Amount (wt.-%) | | | | | | | |
| 8 wt.-% BDDPA in 92 wt.-% Benzyl alcohol | 10 | | | 10 | 10 | | | |
| 2 wt.-% BDDPA in 98 wt.-% Frescolat MPC | | 40 | | | | | | |
| 5 wt.-% BDDPA in 95 wt.-% Anethol | | | 16 | | | 16 | | |
| 5.2 wt.-% BDDPA in 31.6 wt.-% Triethyl citrate + 31.6 wt.-% Triacetin + 31.6 wt.-% Peppermint oil | | | | 16 | | | | |
| 5 wt.-% BDDPA in 47.5 wt.-% Triethyl citrate + 47.5 wt.-% Peppermint oil | | | | | 16 | | | |
| 5 wt.-% BDDPA in 47.5 wt.-% Triacetin + 47.5 wt.-% Frescolat ® ML | | | | | | 16 | 16 | |
| 3 wt.-% BDDPA in 47 wt.-% 2-Phenyl ethanol + 50 wt.-% Frescolat ® MPC | | | | | 40 | | | |
| 10 wt.-% BDDPA in 90 wt.-% Benzyl alcohol | | | | | | | 8 | |
| Solution A | 90 | 60 | 84 | 74 | 44 | 74 | 76 | 84 |
| Total | 100 | 100 | 100 | 100 | 100 | 100 | 100 | 100 |

The aromas obtained in such manner were each added into a standard toothpaste mass based on silica in a concentration of 1.2 wt.-%.

Aroma Composition FM-24:

Production of aromas with a cooling effect and wintergreen taste by using the cooling substances according to the invention.

A solution A with the following composition was mixed with different mixtures according to the invention such that aroma compositions a-h were obtained.

Solution A:

| Component | Amount (wt.-%) |
|---|---|
| Anethol | 10 |
| Peppermint oil *Mentha arvensis* | 12 |
| Peppermint oil *Mentha piperita* type Willamette | 12 |
| Methyl salicylate | 25 |
| l-Menthol | 41 |
| Total | 100 |

| | Aroma composition | | | | | | | |
|---|---|---|---|---|---|---|---|---|
| | a | b | c | d | e | f | g | h |
| | Amount (wt.-%) | | | | | | | |
| 8 wt.-% BDDPA in 92 Wt.-% Benzyl alcohol | 6.25 | | | | | | 6.25 | |
| 2 Wt.-% BDDPA in 98 Wt.-% Frescolat MPC | | 25 | 25 | | | | | |
| 5 Wt.-% BDDPA in 95 Wt.-% Anethol | | | | 10 | | | | |
| 5 Wt.-% BDDPA in 47.5 Wt.-% Triethyl citrate + 47.5 Wt.-% Peppermint oil | | | | | 10 | | | |
| 5.2 Wt.-% BDDPA in 31.6 Wt.-% Triethyl citrate + 31.6 Wt.-% Triacetin + 31.6 Wt.-% Peppermint oil | | | | | | 10 | 10 | |
| 5 Wt.-% BDDPA in 47.5 Wt.-% Triacetin + 47.5 Wt.-% Frescolat ® ML | | | | | | | 10 | 10 |

-continued

| | Aroma composition | | | | | | | |
|---|---|---|---|---|---|---|---|---|
| | a | b | c | d | e | f | g | h |
| | Amount (wt.-%) | | | | | | | |
| 3 Wt.-% BDDPA in 47 Wt.-% 2-Phenyl ethanol + 50 Wt.-% Frescolat ® MPC | | | | | | | 16.5 | |
| 10 wt.-% BDDPA in 90 Wt.-% Benzyl alcohol | | | | | | | | 5 |
| Solution A | 93.75 | 75 | 65 | 80 | 80 | 90 | 77.25 | 95 |
| Total | 100 | 100 | 100 | 100 | 100 | 100 | 100 | 100 |

The aromas obtained in such manner were each added into a standard toothpaste mass based on silica in a concentration of 1.2 wt.-%.

Aroma Composition FM-25:

Production of aromas with a cooling effect and a peppermint taste by using the cooling substances according to the invention:

A solution A with the following composition was mixed with different mixtures according to the invention such that aroma compositions a-h were obtained.

Solution A:

| Component | Amount (wt.-%) |
|---|---|
| Peppermint oil *Mentha arvensis* | 60 |
| I-Menthon | 20 |
| I-Menthol | 20 |
| Total | 100 |

The aromas obtained in such manner were each added into a sugar-free standard chewing gum mass in a concentration of 1.5 wt.-%.

Aroma Composition FM-26:

Production of aromas with a cooling effect and a spearmint taste by using the cooling substances according to the invention:

A solution A with the following composition was mixed with different mixtures according to the invention such that aroma compositions a-h were obtained.

Solution A:

| Component | Amount (wt.-%) |
|---|---|
| Peppermint oil *Mentha piperita* type Madras | 50 |
| Eucalyptol | 20 |
| I-Menthol | 15 |
| I-Menthon | 10 |
| Spearming oil Typ Midwest Scotch | 5 |
| Total | 100 |

| | Aroma composition | | | | | | | |
|---|---|---|---|---|---|---|---|---|
| | a | b | c | d | e | f | g | h |
| | Amount (wt.-%) | | | | | | | |
| 8 wt.-% BDDPA in 92 wt.-% Benzyl alcohol | 10 | | | | 10 | | | |
| 2 wt.-% BDDPA in 98 wt.-% Frescolat MPC | | 40 | | | | | | |
| 5 wt.-% BDDPA in 95 wt.-% Anethol | | | 16 | | | | 16 | |
| 5 wt.-% BDDPA in 47.5 wt.-% Triethyl citrate + 47.5 wt.-% Peppermint oil | | | | 16 | | | | |
| 5.2 wt.-% BDDPA in 31.6 wt.-% Triethyl citrate + 31.6 wt.-% Triacetin + 31.6 wt.-% Peppermint oil | | | | 16 | | | | |
| 5 wt.-% BDDPA in 47.5 wt.-% Triacetin + 47.5 wt.-% Frescolat ® ML | | | | | 16 | | 16 | |
| 3 wt.-% BDDPA in 47 wt.-% 2-Phenyl ethanol + 50 wt.-% Frescolat ® MPC | | | | | | 26.5 | | |
| 10 wt.-% BDDPA in 90 wt.-% Benzyl alcohol | | | | | | | 8 | 8 |
| Solution A | 90 | 60 | 84 | 68 | 74 | 73.5 | 76 | 76 |
| Total | 100 | 100 | 100 | 100 | 100 | 100 | 100 | 100 |

| | Aroma composition | | | | | | | |
|---|---|---|---|---|---|---|---|---|
| | a | b | c | d | e | f | g | h |
| | Amount (wt.-%) | | | | | | | |
| 8 wt.-% BDDPA in 92 wt.-% Benzyl alcohol | 7.5 | | | | | | | |
| 2 wt.-% BDDPA in 98 wt.-% Frescolat MPC | | 30 | | | 30 | | | 30 |
| 5 wt.-% BDDPA in 95 wt.-% Anethol | | | 12 | | | | | |
| 5 wt.-% BDDPA in 47.5 wt.-% Triethyl citrate + 47.5 wt.-% Peppermint oil | | | 12 | | | | | |
| 5.2 wt.-% BDDPA in 31.6 wt.-% Triethyl citrate + 31.6 wt.-% Triacetin + 31.6 wt.-% Peppermint oil | | | | 12 | 12 | | | |
| 5 wt.-% BDDPA in 47.5 wt.-% Triacetin + 47.5 wt.-% Frescolat ® ML | | | | | | 12 | | |
| 3 wt.-% BDDPA in 47 wt.-% 2-Phenyl ethanol + 50 wt.-% Frescolat ® MPC | | | | | | | 20 | |
| 10 wt.-% BDDPA in 90 wt.-% Benzyl alcohol | | | | | | | 6 | 6 |
| Solution A | 92.5 | 58 | 88 | 88 | 58 | 88 | 74 | 64 |
| Total | 100 | 100 | 100 | 100 | 100 | 100 | 100 | 100 |

The aromas obtained in such manner were each added into a sugar-free standard chewing gum mass in a concentration of 1.5 wt.-%.

Aroma Composition FM-27:

Production of aromas with a cooling effect and an aromatic-spicy cinnamon taste by using the cooling substances according to the invention:

A solution A with the following composition was mixed with different mixtures according to the invention such that aroma compositions a-h were obtained.

Solution A:

| Component | Amount (wt.-%) |
|---|---|
| Menthylmethyl ether | 3 |
| Cinnamon aldehyde | 10 |
| Anethol | 10 |
| Eugenol | 2 |
| Peppermint oil *Mentha piperita* Type Madras | 10 |
| Peppermint oil *mentha arvensis* | 10 |
| Spearmint oil Type Midwest Scotch | 10 |
| l-Menthol | 41 |
| 2-Hydroxyethylmenthyl carbonate | 2 |
| 2-Hydroxypropylmenthyl carbonate | 2 |
| Total | 100 |

| | Aroma composition (wt.-%) | | | | | | |
|---|---|---|---|---|---|---|---|
| | a | b | c | d | e | f | g |
| 8 wt.-% BDDPA in 92 wt.-% Benzyl alcohol | 7.5 | | 7.5 | | | | 7.5 |
| 2 wt.-% BDDPA in 98 wt.-% Frescolat MPC | | 30 | | | | | |
| 5 wt.-% BDDPA in 95 wt.-% Anethol | | | | | | | 12 |
| 5 wt.-% BDDPA in 47.5 wt.-% Triethyl citrate + 47.5 wt.-% Peppermint oil | | | | | 12 | | |
| 5.2 wt.-% BDDPA in 31.6 wt.-% Triethyl citrate + 31.6 wt.-% Triacetin + 31.6 wt.-% Peppermint oil | | | | | | 12 | |
| 5 wt.-% BDDPA in 47.5 wt.-% Triacetin + 47.5 wt.-% Frescolat ® ML | | | | 12 | | | |

|  | Aroma composition (wt.-%) | | | | | | |
| --- | --- | --- | --- | --- | --- | --- | --- |
|  | a | b | c | d | e | f | g |
| 3 wt.-% BDDPA in 47 wt.-% 2-Phenyl ethanol + 50 wt.-% Frescolat ® MPC |  |  |  |  |  | 20 |  |
| 10 wt.-% BDDPA in 90 wt.-% Benzyl alcohol |  |  | 6 |  | 6 |  | 6 |
| Solution A | 92.5 | 58 | 86.5 | 76 | 94 | 80 | 74.5 |
| Total | 100 | 100 | 100 | 100 | 100 | 100 | 100 |

The aromas obtained in such manner were each added into a sugar-free standard chewing gum mass in a concentration of 1.5 wt.-%.

Aroma Composition FM-28:

Production of mouthwash aromas with a cooling effect by using the cooling substances according to the invention:

A solution A with the following composition was mixed with different mixtures according to the invention such that aroma compositions a-h were obtained.

Solution A:

| Component | Amount (wt.-%) |
| --- | --- |
| Anethol | 30 |
| Eucalyptol | 25 |
| I-Menthol | 45 |
| Total | 100 |

|  | Aroma composition | | | | | | | |
| --- | --- | --- | --- | --- | --- | --- | --- | --- |
|  | a | b | c | d | e | f | g | h |
|  | Amount (wt.-%) | | | | | | | |
| 8 wt.-% BDDPA in 92 wt.-% Benzyl alcohol | 7.5 |  |  |  |  |  | 7.5 |  |
| 2 wt.-% BDDPA in 98 wt.-% Frescolat MPC |  | 30 |  |  |  |  |  | 30 |
| 5 wt.-% BDDPA in 95 wt.-% Anethol |  |  | 12 | 12 |  | 12 | 12 |  |
| 5 wt.-% BDDPA in 47.5 wt.-% Triethyl citrate + 47.5 wt.-% Peppermint oil |  |  |  | 12 |  |  |  |  |
| 5.2 wt.-% BDDPA in 31.6 wt.-% Triethyl citrate + 31.6 wt.-% Triacetin + 31.6 wt.-% Peppermint oil |  |  |  |  |  | 12 |  | 12 |
| 10 wt.-% BDDPA in 90 wt.-% Benzyl alcohol |  |  |  |  | 6 | 6 | 6 |  |
| Solution A | 92.5 | 70 | 88 | 76 | 94 | 70 | 74.5 | 58 |
| Total | 100 | 100 | 100 | 100 | 100 | 100 | 100 | 100 |

The aromas were each added into a ready-to-use mouthwash with a concentration of 0.15 wt.-% or, respectively, in a mouthwash concentrate with a concentration of 3 wt.-%

The aroma compositions described in Examples FM-21 to FM-28 are suitable for an application in a variety of different finished-products, wherein the application is not limited to toothpastes. An advantageous quickly arising but simultaneously very long lasting feeling of freshness could be perceived in all subsequently described examples, without the feeling of freshness being impaired by hot and bitter impressions.

Subsequently, further application examples for the aroma compositions as mentioned above in further finished-products are described:

Application Example FM-29: Toothpaste ('Silica Opaque')

| | Composition | | | | | |
|---|---|---|---|---|---|---|
| | 1 | 2 | 3 | 4 | 5 | 6 |
| Component | Amount (wt.-%) | | | | | |
| Deionized Water | 26.53 | 26.53 | 26.53 | 26.53 | 26.53 | 26.53 |
| Sorbitol 70% | 45 | Ad 100 | 45 | Ad 100 | 45 | Ad 100 |
| Solbrol M Na-Salt | 0.15 | 0.15 | 0.15 | 0.15 | 0.15 | 0.15 |
| Trisodium phosphate | 0.1 | 0.1 | 0.1 | 0.1 | 0.1 | 0.1 |
| Saccharin | 0.2 | 0.2 | 0.2 | 0.2 | 0.2 | 0.2 |
| Sodium monofluorphosphate | 1.12 | 1.12 | 1.12 | 1.12 | 1.12 | 1.12 |
| PEG 1500 | 5 | 5 | 5 | 5 | 5 | 5 |
| Sident 9 (Abrasive Silica) | 10 | 10 | 10 | 10 | 10 | 10 |
| Sident 22 S (Thickening Silica) | 8 | 8 | 8 | 8 | 8 | 8 |
| Sodium carboxymethylcellulose | 0.9 | 0.9 | 0.9 | 0.9 | 0.9 | 0.9 |
| Titanium (IV) oxide | 0.5 | 0.5 | 0.5 | 0.5 | 0.5 | 0.5 |
| Sodium laurylsulfate (SLS) | 1.5 | 1.5 | 1.5 | 1.5 | 1.5 | 1.5 |
| Pellitorin-Solution PLM (containing 10% Pellitorin) | — | 0.025 | — | 0.025 | — | 0.025 |
| Aroma composition FM-21 (b) | 1 | 1 | | | | |
| Aroma composition FM-21 (c) | | | 1 | 1 | | |
| Aroma composition FM-21 (f) | | | | | 1 | 1 |

Application Example FM-30: Toothpaste (Calcium Carbonate-Base)

| | Composition | | | | | |
|---|---|---|---|---|---|---|
| | 1 | 2 | 3 | 4 | 5 | 6 |
| Component | Amount (wt.-%) | | | | | |
| Saccharin | 0.2 | 0.2 | 0.2 | 0.2 | 0.2 | 0.2 |
| Solbrol M Sodium salt | 0.2 | 0.2 | 0.2 | 0.2 | 0.2 | 0.2 |
| Sodium monofluorphosphate | 0.8 | 0.8 | 0.8 | 0.8 | 0.8 | 0.8 |
| Sorbitol 70% | 29 | 29 | 29 | 29 | 29 | 29 |
| Calcium carbonate | 35 | 35 | 35 | 35 | 35 | 35 |
| Sident 22 S (Thickening Silica) | 2.5 | 2.5 | 2.5 | 2.5 | 2.5 | 2.5 |
| Sodium carboxymethylcellulose | 1.3 | 1.3 | 1.3 | 1.3 | 1.3 | 1.3 |
| Titanium dioxide | 0.5 | 0.5 | 0.5 | 0.5 | 0.5 | 0.5 |
| Sodium laurylsulfate | 2 | 2 | 2 | 2 | 2 | 2 |
| Pellitorin-Solution PLM (containing 10% Pellitorin) | — | 0.02 | — | 0.02 | — | 0.02 |
| Aroma composition FM-21 (a) | 1 | 1 | | | | |
| Aroma composition FM-21 (d) | | | 1 | 1 | | |
| Aroma composition FM-21 (h) | | | | | 1 | 1 |
| Deionized Water | 27.5 | Ad 100 | 27.5 | Ad 100 | 27.5 | Ad 100 |

Application Example FM-31: Toothpaste with Bleaching Effect

| | Composition | | | | | |
|---|---|---|---|---|---|---|
| | 1 | 2 | 3 | 4 | 5 | 6 |
| Component | Amount (wt.-%) | | | | | |
| Polyphosphate (Glass H, (n ≈ 21), Astaris) | 7 | 7 | 7 | 7 | 7 | 7 |
| Calcium peroxide | 1 | — | 2.5 | 1 | — | 2.5 |
| Na-percarbonate | — | 11 | — | — | 11 | — |
| Poloxamer 407 | 5 | 2 | 5 | 5 | 2 | 5 |
| Polyethylene glycol | 3 | — | 3 | 3 | — | 3 |
| Sorbitol, 70% in Water | — | 22 | — | — | 22 | — |
| Glycerine | 43.8 | 12.5 | 28.6 | 43.8 | 12.5 | 28.6 |

-continued

|  | Composition | | | | | |
|---|---|---|---|---|---|---|
|  | 1 | 2 | 3 | 4 | 5 | 6 |
| Component | Amount (wt.-%) | | | | | |
| 1,2-Propylene glycol | 4 | — | 2.5 | 4 | — | 2.5 |
| Na-Saccharin | 0.4 | 0.2 | 0.5 | 0.4 | 0.2 | 0.5 |
| Sodium bicarbonate | — | 5 | 15 | — | 5 | 15 |
| Sodium carbonate | 2 | 2 | 2 | 2 | 2 | 2 |
| Silica | 20 | 22 | 20 | 20 | 22 | 20 |
| Na-Carboxymethylcellulose | 0.6 | 0.55 | 0.3 | 0.6 | 0.55 | 0.3 |
| Sodium laurylsulfate | 1 | 4 | 2 | 1 | 4 | 2 |
| Xanthan Gum | 0.2 | 0.2 | 0.2 | 0.2 | 0.2 | 0.2 |
| Titanium dioxide (Anatas) | 0.5 | 0.5 | 0.5 | 0.5 | 0.5 | 0.5 |
| Aroma composition FM-21 (d) | 1 |  |  |  |  |  |
| Aroma composition FM-21 (g) |  |  |  | 1 |  |  |
| Aroma composition FM-23 (a) |  | 1.25 |  |  |  |  |
| Aroma composition FM-23 (d) |  |  |  |  | 1.25 |  |
| Aroma composition FM-23 (e) |  |  | 1.5 |  |  |  |
| Aroma composition FM-23 (g) |  |  |  |  |  | 1.5 |
| Water dest. | Ad 100 | Ad 100 | Ad 100 | Ad 100 | Ad 100 | Ad 100 |

Application Example FM-32: Toothpastes with Tin Salts and Zinc Salts

|  | Composition | | | | | |
|---|---|---|---|---|---|---|
|  | 1 | 2 | 3 | 4 | 5 | 6 |
| Component | Amount (wt.-%) | | | | | |
| Sodium fluoride NaF | 0.42 | 0.5 | — | 0.42 | 0.5 | — |
| Tin fluoride SnF2 | — | 0.9 | 0.95 | — | 0.9 | 0.95 |
| Tin chloride SnCl2 | 1.5 | — | 2 | 1.5 | — | 2 |
| Zink lactate | 2 | 2 | — | 2 | 2 | — |
| Zink carbonate ZnCO3 | — | 1 | 1.5 | — | 1 | 1.5 |
| Na-gluconate | — | 0.67 | 1.5 | — | 0.67 | 1.5 |
| Poloxamer 407 | 14.5 | — | — | 14.5 | — | — |
| Polyethylene glycol | 1 | 3 | — | 1 | 3 | — |
| Sorbitol, 70% in Water | — | 38 | 37.5 | — | 38 | 37.5 |
| Glycerine | 37.5 | 5 | 14.4 | 37.5 | 5 | 14.4 |
| 1,2-Propylene glycol | 7 | 5 | — | 7 | 5 | — |
| Na-Saccharin | 0.3 | 0.5 | 0.5 | 0.3 | 0.5 | 0.5 |
| Abrasive-Silica | 20 | 22.5 | 25 | 20 | 22.5 | 25 |
| Sodium hydroxide | — | 0.1 | 0.2 | — | 0.1 | 0.2 |
| Sodium laurylsulfate | — | 2 | 1.5 | — | 2 | 1.5 |
| Na-polyphosphate | — | — | 4 | — | — | 4 |
| Tetrasodium pyrophosphate | 1 | 2.5 | — | 1 | 2.5 | — |
| Dye (1% in Water) | 0.4 | 0.5 | 0.5 | 0.4 | 0.5 | 0.5 |
| Aroma composition FM-21 (b) | 0.95 | — | — | — | — | — |
| Aroma composition FM-21 (c) |  |  |  | 0.95 |  |  |
| Aroma composition FM-23 (c) | — | 1.2 | — | — |  | — |
| Aroma composition FM-23 (f) |  |  |  |  | 1.2 |  |
| Aroma composition FM-24 (a) | — | — | 1.15 | — |  |  |
| Aroma composition FM-24 (e) |  |  |  |  |  | 1.15 |
| Water dest. | Ad 100 | Ad 100 | Ad 100 | Ad 100 | Ad 100 | Ad 100 |

Application Example FM-33: Toothpaste on a Phosphate Base

|  | Composition | | | | | |
|---|---|---|---|---|---|---|
|  | 1 | 2 | 3 | 4 | 5 | 6 |
| Component | Amount (wt.-%) | | | | | |
| Glycerine | 20 | 20 | 20 | 20 | 20 | 20 |
| Solbrol M (Sodium salt) | 0.15 | 0.15 | 0.15 | 0.15 | 0.15 | 0.15 |
| Sodium monofluorphosphate | 0.76 | 0.76 | 0.76 | 0.76 | 0.76 | 0.76 |
| Saccharin | 0.2 | 0.2 | 0.2 | 0.2 | 0.2 | 0.2 |
| Dicalciumphosphate-Dihydrate | 36 | 36 | 36 | 36 | 36 | 36 |
| Aerosil ® 200 (Silica) | 3 | 3 | 3 | 3 | 3 | 3 |

|  | Composition | | | | | |
|---|---|---|---|---|---|---|
|  | 1 | 2 | 3 | 4 | 5 | 6 |
| Component | Amount (wt.-%) | | | | | |
| Sodium carboxymethylcellulose | 1.2 | 1.2 | 1.2 | 1.2 | 1.2 | 1.2 |
| Sodium laurylsulfate (Texapon) | 1.3 | 1.3 | 1.3 | 1.3 | 1.3 | 1.3 |
| Aroma composition FM-22 (a) | 1 | | | | | |
| Aroma composition FM-22 (b) | | 1 | | | | |
| Aroma composition FM-22 (d) | | | 0.8 | | | |
| Aroma composition FM-22 (f) | | | | 0.8 | | |
| Aroma composition FM-22 (g) | | | | | 1 | |
| Aroma composition FM-22 (h) | | | | | | 1 |
| Deionized Water | 36.39 | 36.39 | 36.59 | 36.59 | 36.39 | 36.39 |

Application Example FM-34: Toothpaste
(Transparent Yellow Formulation)

|  | Composition | | | | | |
|---|---|---|---|---|---|---|
|  | 1 | 2 | 3 | 4 | 5 | 6 |
| Component | Amount (wt.-%) | | | | | |
| Sorbitol 70% | 63 | Ad 100 | 63 | Ad 100 | 63 | Ad 100 |
| Deionized Water | 11.31 | 11.31 | 11.31 | 11.31 | 11.31 | 11.31 |
| Saccharin | 0.2 | 0.2 | 0.2 | 0.2 | 0.2 | 0.2 |
| Sodium monofluorphosphate | 1.14 | 1.14 | 1.14 | 1.14 | 1.14 | 1.14 |
| Solbrol | 0.15 | 0.15 | 0.15 | 0.15 | 0.15 | 0.15 |
| Trisodium phosphate | 0.1 | 0.1 | 0.1 | 0.1 | 0.1 | 0.1 |
| PEG 1500 (PEG 32) | 5 | 5 | 5 | 5 | 5 | 5 |
| Sident 9 (Abrasive Silica) | 8 | 8 | 8 | 8 | 8 | 8 |
| Sident 22 S (Thickening Silica) | 8 | 8 | 8 | 8 | 8 | 8 |
| Sodium carboxymethylcellulose | 0.6 | 0.6 | 0.6 | 0.6 | 0.6 | 0.6 |
| Sodium laurylsulfate | 1.5 | 1.5 | 1.5 | 1.5 | 1.5 | 1.5 |
| Pellitorin-Solution PLM (containing 10% Pellitorin) | — | 0.025 | — | 0.025 | — | 0.025 |
| Aroma composition FM-23 (c) | 1 | — | | | | |
| Aroma composition FM-23 (e) | | 1 | | | | |
| Aroma composition FM-23 (h) | | | 1 | | | |
| Aroma composition FM-24 (b) | — | | | 1 | | |
| Aroma composition FM-24 (d) | | | | | 1 | |
| Aroma composition FM-24 (g) | | | | | | 1 |

Application Example FM-35: Mouthwash
Concentrate with Aroma of Wintergreen Type

|  | Composition | | | | | |
|---|---|---|---|---|---|---|
|  | 1 | 2 | 3 | 4 | 5 | 6 |
| Component | Amount (wt.-%) | | | | | |
| Ethyl alcohol 96% | 42 | 42 | 42 | 42 | 42 | 42 |
| Cremophor RH 455 | 5 | 5 | 5 | 5 | 5 | 5 |
| Deionized Water | 48.67 | 48.67 | 50.67 | 49.67 | 48.67 | 48.67 |
| Allantoin | 0.2 | 0.2 | 0.2 | 0.2 | 0.2 | 0.2 |
| Sodium saccharin 450 | 0.1 | 0.1 | 0.1 | 0.1 | 0.1 | 0.1 |
| Colour L-Blue 5000 (1% in Water) | 0.03 | 0.03 | 0.03 | 0.03 | 0.03 | 0.03 |
| Aroma composition FM-24 (b) | 4 | | | | | |
| Aroma composition FM-24 (c) | | 4 | | | | |
| Aroma composition FM-24 (d) | | | 2 | | | |
| Aroma composition FM-24 (e) | | | | 3 | | |
| Aroma composition FM-24 (f) | | | | | 4 | |
| Aroma composition FM-24 (h) | | | | | | 4 |

Application Example FM-36: Mouthwash
(Ready-to-Use without Alcohol)

| Component | Composition | | | | | |
|---|---|---|---|---|---|---|
| | 1 | 2 | 3 | 4 | 5 | 6 |
| | Amount (wt.-%) | | | | | |
| Cremophor RH 455 | 1.8 | 1.8 | 1.8 | 1.8 | 1.8 | 1.8 |
| Sorbitol 70% | 10 | 10 | 10 | 10 | 10 | 10 |
| Sodium fluoride | 0.18 | 0.18 | 0.18 | 0.18 | 0.18 | 0.18 |
| Sodium saccharin 450 | 0.1 | 0.1 | 0.1 | 0.1 | 0.1 | 0.1 |
| Solbrol M Sodium salt | 0.15 | 0.15 | 0.15 | 0.15 | 0.15 | 0.15 |
| Pellitorin-solution PLM (containing 10% Pellitorin) | — | 0.0125 | — | 0.0125 | — | 0.0125 |
| Aroma composition FM-28 (a) | 0.2 | 0.2 | | | | |
| Aroma composition FM-28 (d) | | | 0.2 | 0.2 | | |
| Aroma composition FM-28 (g) | | | | | 0.2 | 0.2 |
| Deionized Water | 87.57 | Ad 100 | 87.57 | Ad 100 | 87.57 | Ad 100 |

Application Example FM-37: Mouthwash
(Ready-to-Use with Alcohol)

| Component | Composition | | | | | |
|---|---|---|---|---|---|---|
| | 1 | 2 | 3 | 4 | 5 | 6 |
| | Amount (wt.-%) | | | | | |
| Ethyl alcohol 96% | 10 | 5 | 7 | 10 | 5 | 7 |
| Cremophor CO 40 | 1 | 1 | 1 | 1 | 1 | 1 |
| Benzoic acid | 0.1 | 0.12 | 0.1 | 0.1 | 0.12 | 0.1 |
| Sorbitol 70% | 5 | 1 | 5 | 5 | 1 | 5 |
| Sodium saccharin 450 | 0.07 | 0.05 | 0.05 | 0.07 | 0.05 | 0.05 |
| L-Blue 5000 (1% in Water) | 0.1 | 0.1 | 0.1 | 0.1 | 0.1 | 0.1 |
| Glycerine | — | 8 | — | — | 8 | — |
| 1,2-Propylene glycol | — | 2 | 3 | — | 2 | 3 |
| Cetylpyridinium chloride | — | — | 0.07 | — | — | 0.07 |
| Hydrogen peroxide (35% H2O2 in water) | — | 3 | 4 | — | 3 | 4 |
| Aroma composition FM-24 (d) | 0.25 | — | — | — | — | — |
| Aroma composition FM-24 (h) | | | | 0.25 | | |
| Aroma composition FM-28 (b) | — | 0.25 | 0.25 | | | |
| Aroma composition FM-28 (c) | | | | | 0.25 | 0.25 |
| Deionized Water | 83.8 | Ad 100 | Ad 100 | 83.8 | Ad 100 | Ad 100 |

Application Example FM-38: Toothpaste and
Mouthwash as 2-in-1 Product

| Component | Composition | | | | | |
|---|---|---|---|---|---|---|
| | 1 | 2 | 3 | 4 | 5 | 6 |
| | Amount (wt.-%) | | | | | |
| Ethanol, 96% | 5 | 5 | 5 | 5 | 5 | 5 |
| Sorbitol, 70% in Water | 40 | 40 | 40 | 40 | 40 | 40 |
| Glycerine | 20 | 20 | 20 | 20 | 20 | 20 |
| Saccharin | 0.2 | 0.2 | 0.2 | 0.2 | 0.2 | 0.2 |
| Na-Monofluorphosphate | 0.76 | 0.76 | 0.76 | 0.76 | 0.76 | 0.76 |
| Solbrol M, Na-Salt | 0.15 | 0.15 | 0.15 | 0.15 | 0.15 | 0.15 |
| Abrasive silica (Sident 9) | 20 | 20 | 20 | 20 | 20 | 20 |
| Thickening silica (Sident 22S) | 2 | 2 | 2 | 2 | 2 | 2 |
| Na-Carboxymethylcellulose | 0.3 | 0.3 | 0.3 | 0.3 | 0.3 | 0.3 |
| Sodium laurylsulfate | 1.2 | 1.2 | 1.2 | 1.2 | 1.2 | 1.2 |
| Green dye (1ig in Water) | 0.5 | 0.5 | 0.5 | 0.5 | 0.5 | 0.5 |
| Aroma composition FM-21 (a) | 1 | | | | | |
| Aroma composition FM-21 (b) | | 1 | | | | |
| Aroma composition FM-21 (c) | | | 1 | | | |
| Aroma composition FM-21 (e) | | | | 1 | | |

-continued

|  | Composition | | | | | |
|---|---|---|---|---|---|---|
| Component | 1 | 2 | 3 | 4 | 5 | 6 |
|  | Amount (wt.-%) | | | | | |
| Aroma composition FM-21 (f) |  |  |  |  | 1 |  |
| Aroma composition FM-21 (h) |  |  |  |  |  | 1 |
| Water dest. | Ad 100 | Ad 100 | Ad 100 | Ad 100 | Ad 100 | Ad 100 |

Application Example FM-39: Standard Chewing Gum

|  | Composition | | | | | |
|---|---|---|---|---|---|---|
| Component | 1 | 2 | 3 | 4 | 5 | 6 |
|  | Amount (wt.-%) | | | | | |
| Gum Base | 21 | 21 | 21 | 21 | 21 | 21 |
| Glucose syrup | 16.5 | 17 | 16.5 | 16.5 | 17 | 16.5 |
| Glycerine | 0.5 | 0.5 | 0.5 | 0.5 | 0.5 | 0.5 |
| Sugar, powdered | 60 | 60 | 60 | 60 | 60 | 60 |
| Aroma composition FM-25 (b) | 2 | — |  |  |  |  |
| Aroma composition FM-25 (c) |  | 1.5 |  |  |  |  |
| Aroma composition FM-25 (h) |  |  | 2 |  |  |  |
| Aroma composition FM-26 (c) | — |  |  | 2 |  |  |
| Aroma composition FM-26 (d) |  |  |  |  | 1.5 |  |
| Aroma composition FM-26 (g) |  |  |  |  |  | 2 |

Application Example FM-40: Sugar-Free Chewing Gum

|  | Composition | | | | | |
|---|---|---|---|---|---|---|
| Component | 1 | 2 | 3 | 4 | 5 | 6 |
|  | Amount (wt.-%) | | | | | |
| Gum Base | 30 | 30 | 30 | 30 | 30 | 30 |
| Isomalt powdered | 9.5 | 9.5 | 9.5 | 9.5 | 9.5 | 9.5 |
| Xylitol | 2 | 2 | 2 | 2 | 2 | 2 |
| Mannit D | 3 | 3 | 3 | 3 | 3 | 3 |
| Aspartame | 0.1 | 0.1 | 0.1 | 0.1 | 0.1 | 0.1 |
| Acesulfam K | 0.1 | 0.1 | 0.1 | 0.1 | 0.1 | 0.1 |
| Emulgum™ (Soja-Lecithine with high amount of phospholipids) | 0.3 | 0.3 | 0.3 | 0.3 | 0.3 | 0.3 |
| Sorbitol (70 in Water) | 13 | 13 | 13 | 13 | 13 | 13 |
| 1,2-Propylene glycol | — | 1 | — | 1 | — | 1 |
| Glycerine | 1 | — | 1 | — | 1 | — |
| Pellitorin-solution PLM (containing 10% Pellitorin) | — | 0.035 | — | 0.035 | — | 0.035 |
| Aroma composition FM-25 (a) | 1 | 1 |  |  |  |  |
| Aroma composition FM-25 (d) |  |  | 0.8 | 0.8 |  |  |
| Aroma composition FM-25 (f) |  |  |  |  | 1 | 1 |
| Sorbit powdered | 40 | Ad 100 | 40.2 | Ad 100 | 40 | Ad 100 |

Application Example FM-41: Chewing Gums (with Sugar and Sugar-Free)

|  | Composition | | | | | |
|---|---|---|---|---|---|---|
| Component | 1 | 2 | 3 | 4 | 5 | 6 |
|  | Amount (wt.-%) | | | | | |
| Gum Base | 21 | 30 | 21 | 30 | 21 | 30 |
| Glycerine | 0.5 | 1 | 0.5 | 1 | 0.5 | 1 |
| Glucose syrup | 16.5 | — | 16.5 | — | 16.5 | — |
| Palatinite | — | 9.5 | — | 9.5 | — | 9.5 |

-continued

| Component | Composition | | | | | |
|---|---|---|---|---|---|---|
| | 1 | 2 | 3 | 4 | 5 | 6 |
| | Amount (wt.-%) | | | | | |
| Xylitol | — | 2 | — | 2 | — | 2 |
| Mannitol | — | 3 | — | 3 | — | 3 |
| Aspartame | — | 0.1 | — | 0.1 | — | 0.1 |
| Acesulfam K | — | 0.1 | — | 0.1 | — | 0.1 |
| EmulgumTM (emulsifier) | — | 0.3 | — | 0.3 | — | 0.3 |
| Sorbitol 70%, in Water | — | 14 | — | 14 | — | 14 |
| Aroma composition FM-26 (a) | 1 | 1.4 | | | | |
| Aroma composition FM-26 (f) | | | 0.8 | 1.2 | | |
| Aroma composition FM-26 (h) | | | | | 1 | 1.4 |
| Powdered sugar | Ad 100 | — | Ad 100 | — | Ad 100 | — |
| Sorbitol (in form of powder) | — | Ad 100 | — | Ad 100 | — | Ad 100 |

Application Example FM-42: Sugar-Free Chewing Gums

The gum base K1 consisted of 2.0% butyl rubber (Isobuten-Isopren-Copolymer, MW=400000, 6.0% Polyisobuten (MW=43.800), 43.5% Polyvinyl acetate (MW=12.000), 31.5% Polyvinyl acetate (MW=47.000), 6.75% Triacetin and 10.25% Calcium carbonate. The production of the gum base K1 and the chewing gums can be performed analogously to U.S. Pat. No. 5,601,858.

| Component | Composition | | | | | |
|---|---|---|---|---|---|---|
| | 1 | 2 | 3 | 4 | 5 | 6 |
| | Amount (wt.-%) | | | | | |
| Gum base K1 | 26 | 27 | 26 | 26 | 27 | 26 |
| Triacetin | 0.25 | 0.25 | 0.25 | 0.25 | 0.25 | 0.25 |
| Lecithine | 0.5 | 0.5 | 0.5 | 0.5 | 0.5 | 0.5 |
| Mannitol | 15.3 | 15.2 | 15.1 | 15.3 | 15.2 | 15.1 |
| Glycerine | 12.1 | 12 | 11.8 | 12.1 | 12 | 11.8 |
| Saccharin-Na | 0.17 | — | 0.1 | 0.17 | — | 0.1 |
| Capsuled Aspartam | 1.08 | 1.18 | 1.08 | 1.08 | 1.18 | 1.08 |
| Amorphous Silica | 1 | 1 | 1 | 1 | 1 | 1 |
| Cotton seed oil | 0.5 | 0.5 | 0.5 | 0.5 | 0.5 | 0.5 |
| Polyoxy ethylene-sorbitan-monolaurate (E-432) | 1 | 1 | 1 | 1 | 1 | 1 |
| Capsuled l-Carvone (Load: 30%) | — | 0.2 | — | — | 0.2 | — |
| l-Menthyl-l-lactate | — | — | 0.2 | — | — | 0.2 |
| Aroma composition FM-26 (c) | 1 | — | 1.7 | | | |
| Aroma composition FM-26 (d) | | | | 0.8 | — | 1.4 |
| Aroma composition FM-25 (b) | 0.5 | 1.4 | — | | | |
| Aroma composition FM-25 (e) | | | | 0.5 | 1.4 | — |
| Sorbitol, crystalline | Ad 100 | Ad 100 | Ad 100 | Ad 100 | Ad 100 | Ad 100 |

Application Example FM-43: Sugar-Free Chewing Gums

The gum base K2 consisted of 28.5% Terpene resin, 33.9% Polyvinyl acetate (MW=14.000), 16.25% hydrated vegetable oil, 5.5% Mono- and Diglycerides, 0.5% Polyisobutene (MW 75.000), 2.0% Butyl Rubber (Isobutene-Isopren-Copolymer), 4.6% amorphous Silicon dioxide (Water content approx. 2.5%), 0.05% Antioxidant tert.-Butylhydroxy toluene (BHT), 0.2% lecitihine, and 8.5% Calcium carbonate. The production of the gum base K2 and the chewing gums can be performed analogously to U.S. Pat. No. 6,986,907.

| Component | Composition | | | | | |
|---|---|---|---|---|---|---|
| | 1 | 2 | 3 | 4 | 5 | 6 |
| | Amount (wt.-%) | | | | | |
| Gum base K2 | 25.3 | 27.3 | 26.3 | 25.3 | 27.3 | 26.3 |
| Glycerine | 2.4 | 2.4 | 2.4 | 2.4 | 2.4 | 2.4 |
| Lecithine | 7 | 7 | 7 | 7 | 7 | 7 |
| Aspartame | 0.14 | 0.14 | 0.14 | 0.14 | 0.14 | 0.14 |
| Capsuled Aspartam | 0.68 | 0.68 | 0.68 | 0.68 | 0.68 | 0.68 |

-continued

| Component | Composition | | | | | |
|---|---|---|---|---|---|---|
| | 1 | 2 | 3 | 4 | 5 | 6 |
| | Amount (wt.-%) | | | | | |
| Menthol, spray dried (Load: 25%) | 0.5 | — | 0.5 | 0.5 | — | 0.5 |
| Cherry aroma, spray dried (contains Benzaldehyde) | — | 1 | — | — | 1 | — |
| Aroma composition FM-25 (b), spray dried | 1.5 | 1.7 | — | | | |
| Aroma composition FM-25 (c), spray dried | | | | 1.5 | 1.7 | |
| Aroma composition FM-27 (c) | 1 | — | 1.5 | | | |
| Aroma composition FM-27 (h) | | | | 1 | — | 1.5 |
| Sorbitol | Ad 100 | Ad 100 | Ad 100 | Ad 100 | Ad 100 | Ad 100 |

The chewing gums of recipes (1) and (2) were produced as stripes, those of recipe (3) were produced as compactates in form of a pillow and were subsequently processed with xylit.

Application Example FM-44: Production of Aromas with a Cooling Effect of the Taste Type "Ice Candy" by Using the Cooling Substances According to the Invention

| Component | Composition | | | | | | | |
|---|---|---|---|---|---|---|---|---|
| | a | b | c | d | e | f | g | h |
| | Amount (wt.-%) | | | | | | | |
| Isoamyl acetate | 2 | 2 | 2 | 2 | 2 | 2 | 2 | 2 |
| Ethyl butyrate | 0.5 | — | 0.5 | — | 0.5 | — | 0.5 | — |
| Butyl butyrate | — | 0.5 | — | 0.5 | — | 0.5 | — | 0.5 |
| Ethyl vanilline | 2 | — | 2 | — | 2 | — | 2 | — |
| Vanilline | — | 1 | — | 1 | — | 1 | — | 1 |
| FrambinonTM [4-(4-Hydroxyphenyl)-2-butanone] | 0.5 | 0.5 | 0.5 | 0.5 | 0.5 | 0.5 | 0.5 | 0.5 |
| l-Menthol | 5 | 5 | 5 | 5 | 5 | 5 | 5 | 5 |
| Peppermint oil Type piperita | 6 | 6 | 6 | 6 | 6 | 6 | 6 | 6 |
| Triacetine | — | 84 | — | 84.5 | — | 84.5 | — | 84 |
| 1,2-Propylene glycol | 83 | — | 83.5 | — | 83.5 | — | 83 | — |
| 8 wt.-% BDDPA in 92 wt.-% Benzyl alcohol | 0.5 | 0.5 | | | | | | |
| 2 wt.-% BDDPA in 98 wt.-% Frescolat MPC | 0.5 | 0.5 | | | | | | |
| 5 wt.-% BDDPA in 95 wt.-% Anethol | | | 0.5 | 0.5 | 0.2 | 0.2 | | |
| 5 wt.-% BDDPA in 47.5 wt.-% Triethyl citrate + 47.5 wt.-% Peppermint oil | | | | | 0.3 | 0.3 | | |
| 5 wt.-% BDDPA in 31.6 wt.-% Triethyl citrate + 31.6 wt.-% Triacetin + 31.6 wt.-% Peppermint oil | | | | | | | 0.5 | 0.5 |
| 3 wt.-% BDDPA in 47 wt.-% 2-Phenyl ethanol + 50 wt.-% Frescolat ® MPC | | | | | | | 0.5 | 0.5 |

The aromas were added into different candy masses with concentrations ranging from 0.15 to 0.2 wt.-%.

Application Example FM-45: Candy ('Hardboiled Candy'), Sugar-Free

| Component | Composition | | | | | |
|---|---|---|---|---|---|---|
| | 1 | 2 | 3 | 4 | 5 | 6 |
| | Amount (wt.-%) | | | | | |
| Water | 2.24 | 2.24 | 2.24 | 2.24 | 2.24 | 2.24 |
| Isomalt | 94.98 | Ad 100 | Ad 100 | 94.98 | Ad 100 | Ad 100 |
| Xylitol | 2.4 | 2.4 | 2.4 | 2.4 | 2.4 | 2.4 |
| Sucralose | 0.03 | 0.03 | 0.03 | 0.03 | 0.03 | 0.03 |
| Acesulfam K | 0.05 | 0.05 | 0.05 | 0.05 | 0.05 | 0.05 |
| Citric acid | 0.05 | 0.05 | 0.05 | 0.05 | 0.05 | 0.05 |
| Pellitorin-solution PLM (containing 10% Pellitorin) | — | 0.0075 | 0.01 | — | 0.0075 | 0.01 |
| Aroma composition FM-21 (c) | 0.25 | 0.2 | | | | |
| Aroma composition FM-21 (d) | | | | 0.25 | 0.2 | |
| Aroma Type Ice candy (Example FM-44 (a)) | | | 0.25 | | | |
| Aroma Type Ice candy (Example FM-44 (e)) | | | | | | 0.2 |

Application Example FM-46: Candy ('Hardboiled Candy')

| Component | Composition | | | | | |
|---|---|---|---|---|---|---|
| | 1 | 2 | 3 | 4 | 5 | 6 |
| | Amount (wt.-%) | | | | | |
| Water | 2.75 | 2.5 | 2.5 | 2.75 | 2.5 | 2.5 |
| Sugar | 60.1 | Ad 100 | Ad 100 | 60.1 | Ad 100 | Ad 100 |
| Glucose syrup | 36.9 | 36 | 36 | 36.9 | 36 | 36 |
| Maltose | — | 2 | 2 | — | 2 | 2 |
| Palm kernel oil | — | 0.8 | 0.8 | — | 0.8 | 0.8 |
| Citric acid | — | 0.25 | 0.25 | — | 0.25 | 0.25 |
| Ginseng Extract | — | 0.4 | 0.4 | — | 0.4 | 0.4 |
| Blue dye | — | 0.01 | 0.01 | — | 0.01 | 0.01 |
| Aroma composition FM-22 (a) | 0.25 | 0.35 | — | | | |
| Aroma composition FM-22 (d) | | | | 0.25 | 0.35 | — |
| Aroma Type ice candy (Example FM-44 (b)) | | | 0.175 | | | |
| Aroma Type Ice candy (Example FM-44 (d)) | | | | | | 0.175 |

Application Example FM-47: Instant-Drink Powder

| Component | Composition | | | | | |
|---|---|---|---|---|---|---|
| | 1 | 2 | 3 | 4 | 5 | 6 |
| | Amount (wt.-%) | | | | | |
| Citric acid | 11.58 | 11.58 | 11.58 | 11.58 | 11.58 | 11.58 |
| Trisodium citrate | 0.7 | 0.7 | 0.7 | 0.7 | 0.7 | 0.7 |
| Tricalcium phosphate | 0.6 | 0.6 | 0.6 | 0.6 | 0.6 | 0.6 |
| Vitamin C | 0.66 | 0.66 | 0.66 | 0.66 | 0.66 | 0.66 |
| Grindsted ® JU 543 Stabilizer System (Danisco) | 0.9 | 0.9 | 0.9 | 0.9 | 0.9 | 0.9 |
| Saccharin | 0.561 | 0.561 | 0.561 | 0.561 | 0.561 | 0.561 |
| Lemon aroma, spray dried | 1.75 | — | 1.75 | — | 1.75 | — |
| Orange aroma, spry dried | | 1.85 | | 1.85 | | 1.85 |
| Aroma composition FM-21 (a), spray dried on maltodextrin (DE 15-19) and Gum Arabicum, Aroma load 40% | 1.75 | | | | | |

-continued

| | Composition | | | | | |
|---|---|---|---|---|---|---|
| Component | 1 | 2 | 3 | 4 | 5 | 6 |
| | Amount (wt.-%) | | | | | |
| Aroma composition FM-21 (c), spray dried on maltodextrin (DE 15-19) and Gum Arabicum, Aroma load 40% | | | 1.75 | | | |
| Aroma composition FM-21 (h), spray dried on maltodextrin (DE 15-19) and Gum Arabicum, Aroma load 40% | | | | | 1.75 | |
| Aroma composition FM-23 (b), spray dried on maltodextrin (DE 15-19) and Gum Arabicum, Aroma load 40% | | 1.2 | | | | |
| Aroma composition FM-23 (d), spray dried on maltodextrin (DE 15-19) and Gum Arabicum, Aroma load 40% | | | | 1.2 | | |
| Aroma composition FM-23 (e), spray dried on maltodextrin (DE 15-19) and Gum Arabicum, Aroma load 40% | | | | | | 1.2 |
| Sugar (Saccharose) | Ad 100 | Ad 100 | Ad 100 | Ad 100 | Ad 100 | Ad 100 |

45 g of these instant-drink powders were each dissolved in 1000 mL while stirring.

Application Example FM-48: Throat Lozenge with Liquid-Viscous Core Filling (Centre-Filled Hard Candy)

| | Composition | | | | | |
|---|---|---|---|---|---|---|
| Component | 1 | 2 | 3 | 4 | 5 | 6 |
| | Amount (wt.-%) | | | | | |
| Mixture A (Shell) (80% of the candies) | | | | | | |
| Sugar (Saccharose) | 58.1 | 58.1 | 58.1 | 49.11 | 49.11 | 49.11 |
| Glucose syrup (solid content 80%) | 41.17 | 41.17 | 41.17 | 49.11 | 49.11 | 49.11 |
| Aroma composition FM-23 (a) | 0.17 | 0.17 | 0.17 | 0.25 | 0.25 | 0.25 |
| Aroma composition FM-23 (c) | 0.17 | 0.17 | 0.17 | 0.25 | 0.25 | 0.25 |
| Aroma composition FM-23 (f) | 0.17 | 0.17 | 0.17 | 0.25 | 0.25 | 0.25 |
| tr.-Pellitorin 10% in Propylene glycol/Peppermint oil (1:1) | 0.02 | 0.02 | 0.02 | 0.03 | 0.03 | 0.03 |
| l-Menthol | 0.1 | 0.1 | 0.1 | — | — | — |
| Lemon oil | 0.1 | 0.1 | 0.1 | 0.1 | 0.1 | 0.1 |
| Citric acid | — | — | — | 0.9 | 0.9 | 0.9 |
| Total: | 100 | 100 | 100 | 100 | 100 | 100 |
| Mixture B (Core) (20% of the candies) | | | | | | |
| High Fructose Maize syrup (Amount of solid sugars 85%, approx. 15% water) | 83.795 | 83.795 | 83.795 | 36 | 36 | 36 |
| Glycerine | 15 | 15 | 15 | 15 | 15 | 15 |
| Lecithine | 0.02 | 0.02 | 0.02 | 0.02 | 0.02 | 0.02 |
| Cinnamon oil | — | — | — | 0.27 | 0.27 | 0.27 |
| Aroma composition FM-22 (b) | 0.28 | 0.28 | 0.28 | — | — | — |
| Aroma composition FM-22 (d) | 0.28 | 0.28 | 0.28 | — | — | — |
| Aroma composition FM-22 (g) | 0.28 | 0.28 | 0.28 | — | — | — |
| Capsaicin | 0.025 | 0.025 | 0.025 | — | — | — |
| Piperin | 0.05 | 0.05 | 0.05 | 0.05 | 0.05 | 0.05 |

-continued

| | Composition | | | | | |
|---|---|---|---|---|---|---|
| | 1 | 2 | 3 | 4 | 5 | 6 |
| Component | Amount (wt.-%) | | | | | |
| Vanillyl alcohol-n-butylether | — | — | — | 0.1 | 0.1 | 0.1 |
| Red dye as 2.5% aqueous solution | 0.2 | 0.2 | 0.2 | 0.2 | 0.2 | 0.2 |
| Vanillin | 0.07 | 0.07 | 0.07 | — | — | — |
| Total | 100 | 100 | 100 | 100 | 100 | 100 |

Following the methods described in U.S. Pat. No. 6,432,441 (there: Example 1) as well as U.S. Pat. No. 5,458,894 or respectively U.S. Pat. No. 5,002,791, candies with liquid-viscous core were produced. Both mixtures A and B were processed separately from each other to bases for shell (mixture A) or core (mixture B). The filled throat lozenges obtained by co-extrusion had an effect against cough, sore throat and hoarseness for affected people when consumed.

Application Example FM-49: Gelatine Capsules Suitable for Direct Consumption

| | Composition | |
|---|---|---|
| | 1 | 2 |
| Component | Amount (wt.-%) | Amount (wt.-%) |
| Gelatine shell: | | |
| Glycerine | 2.014 | 2.014 |
| Gelatine 240 Bloom | 7.91 | 7.91 |
| Sucralose | 0.070 | 0.070 |
| Allura Red (red dye) | 0.006 | 0.006 |
| Brillant Blue (blue dye) | 0.005 | 0.005 |
| Core composition: | | |
| Aroma composition FM-21 (a) | 15 | |
| Aroma composition FM-21 (b) | | 15 |
| Vegetable oil triglycerides (coconut oil fraction) | Ad 100 | Ad 100 |

The gelatine capsules suitable for direct consumption were produced according to WO 2004/050069 and had a diameter of 5 mm; the weight ratio of core material to shell material was 90:10.

Application Example FM-50

Production of chewy sweets with a cooling raspberry taste by using the cooling substances according to the invention

| | Composition | | | | | |
|---|---|---|---|---|---|---|
| | 1 | 2 | 3 | 4 | 5 | 6 |
| Component | Amount (wt.-%) | | | | | |
| Water | 7.8 | 7.79 | 7.805 | 7.8 | 7.815 | 7.81 |
| Refined sugar C4 | 42.1 | 42.1 | 42.1 | 42.1 | 42.1 | 42.1 |
| Glucose Syrup Dextrose 40 | 37.3 | 37.3 | 37.3 | 37.3 | 37.3 | 37.3 |
| Hardened vegetable fat melting point 32-36° C. | 6.6 | 6.6 | 6.6 | 6.6 | 6.6 | 6.6 |
| Lecithin emulsifier (Sojalecithin) | 0.3 | 0.3 | 0.3 | 0.3 | 0.3 | 0.3 |
| Gelatine (porine gelatine) | 0.8 | 0.8 | 0.8 | 0.8 | 0.8 | 0.8 |
| Fondant Type - S30 | 4.8 | 4.8 | 4.8 | 4.8 | 4.8 | 4.8 |
| Raspberry aroma | 0.22 | 0.22 | 0.22 | 0.22 | 0.22 | 0.22 |
| Menthyl lactate | 0.06 | 0.06 | 0.06 | 0.06 | 0.06 | 0.06 |
| 8 wt.-% BDDPA in 92 wt.-% Benzyl alcohol | 0.02 | | | | | |
| 2 wt.-% BDDPA in 98 wt.-% Frescolat MPC | | 0.03 | | | | |
| 5.2 wt.-% BDDPA in 31.6 wt.-% Triethyl citrate + 31.6 wt.-% Triacetin + 31.6 wt.-% Peppermint oil | | | 0.015 | | | |
| 5 wt.-% BDDPA in 95 wt.-% Anethol | | | | 0.02 | | |
| 3 wt.-% BDDPA in 47 wt.-% 2-Phenyl ethanol + 50 wt.-% Frescolat ® MPC | | | | | 0.005 | |
| 5 wt.-% BDDPA in 47.5 wt.-% Triacetin + 47.5 wt.-% Frescolat ® ML | | | | | | 0.01 |

Manufacture information:
a) Let the gelatine swell with water (1.8 fold amount of gelatine) at 70° C. for 2 hours;
b) Boil sugar, syrup, water, fat and lecithine at 123° C.;
c) Slowly mix the gelatine solution with the boiled mixture;
d) Stir in the raspberry flavour, the menthyl lactate and the cooling substances according to the invention and optionally the dye;
e) Temper the resulting mass on a cooling table to approximately 70° C., subsequently add fondant and ventilate on a drawing machine for approximately 3 minutes;
f) Subsequently cut and pack the chewy sweet mass.

Application Example FM-51

Production of an extrudate for the provision of drink mixtures with a cooling effect
Unless stated otherwise, all indications in wt.-%

| | Composition | | |
|---|---|---|---|
| Component | 1 Amount (wt.-%) | 2 Amount (wt.-%) | 3 Amount (wt.-%) |
| Glucose syrup, spray dried (DE-value: 31-34) [Glucidex IT33W (company Roquette)] | 62.0 | 62.0 | 62.0 |
| Maltodextrin (DE-value: 17-20), company Cerestar | 28.4 | 28.4 | 28.4 |
| Emulsifier Monomuls, Emulsifier on the basis of hardened palm il; meltin point: 64° C. (company Grunau) | 1.8 | 1.8 | 1.8 |
| Dextrose monohydrate (DE-value: 99.5), company Cerestar | 1.8 | 1.8 | 1.8 |
| Water | 2.0 | 2.0 | 2.0 |
| Orange-Vanilla aroma | 3.2 | 3.2 | 3.2 |
| Aroma composition FM-21 (a) | 0.8 | | |
| Aroma composition FM-21 (b) | | 0.8 | |
| Aroma composition FM-21 (f) | | | 0.8 |

Manufacture information (see also WO 03/092412):
All components were mixed and moved in a twin-screw extruder via one-point dosage. The extrusion temperatures were between 100 and 120° C., the specific energy input was 0.2 kWh/kg. The strands emerging from the nozzle plate which was configured with 1 mm bores were cut by rotating knifes to particles with approx. 1 mm diameter directly after emerging the nozzles.

Application Example FM-52

Production of fluid bed granules for the provision of drink mixtures with a cooling effect
In a granuling apparatus of the type shown in EP 163 836 (with the following features: diameter inflow ground: 225 mm, spray nozzle: two-substance nozzle; classifying discharge: Zig-Zag classifier; filter: internal bag filter), a solution consisting of 44 wt.-% water, 8 wt.-% lemon aroma, 3 wt.-% aroma composition FM-21 (a) to (h), 13 wt.-% Gum arabicum and 32 wt.-% hydrolysed starch (Maltodextrin DE 15-19) as well as some green dye was granule. The solution is sprayed at a temperature of 32° C. into the fluid bed granulator. For fluidizing the bed content, nitrogen in an amount of 140 kg/h is blown in. The inlet temperature of the fluidizing gas is 140° C. The temperature of the output gas is 76° C. As classifying gas, also nitrogen is added in an Amount of 15 kg/h with a temperature of 50° C. The content of the fluid bed is approx. 500 g. The granule performance is 1.5 kg per hour. A free flowing granulate with a middle particle diameter of 360 micrometres is obtained. The granulates are round and have a smooth surface. Due to the constant pressure loss of the filter and of the also constant remaining bed content, stationary conditions with regard to the granulation process can be assumed.

Application Example FM-53

Production of tee bags with rooibos or, respectively, black tee and extrudates of example S-31 or, respectively, granules of example S-32 for the provision of tee drinks with a cooling effect.
Each, 800 g redbush tea (rooibos-tea) were mixed with either 33 g of the extrudates of example FM-51 or 30 g granules of application example FM-52, portioned and filled into tea bags subsequently.
Each, 800 g black tea (Blattgrad Fannings) were mixed with either 33 g of the extrudates of example S-51 or 30 g granules of application example FM-52, portioned and filled into tea bags subsequently.

Application Example FM-54

Production of a sugar containing or, respectively, sugar-reduced ice cream with a long lasting cooling effect by using the cooling substances according to the invention

| | Composition | | | | | |
|---|---|---|---|---|---|---|
| | 1 | 2 | 3 | 4 | 5 | 6 |
| Component | Amount (wt.-%) | | | | | |
| Skimmed milk | 56.75 | 60.55 | 56.75 | 60.55 | 56.75 | 60.55 |
| Vegetable fat, Melting range 35-40° C. | 20 | 20 | 20 | 20 | 20 | 20 |
| Sugar (Saccharose) | 12 | 8 | 12 | 8 | 12 | 8 |
| Skimmed milk powder | 5 | 5 | 5 | 5 | 5 | 5 |
| Glucose syrup 72% dry matter | 5 | 5 | 5 | 5 | 5 | 5 |
| Emulsifier SE 30 (Grindstedt Products. Denmark) | 0.65 | 0.65 | 0.65 | 0.65 | 0.65 | 0.65 |
| Vanilla aroma, containing 1% Vanillin and 2.5% of a composition of BDDPA (8 wt.-%) + Benzyl alcohol (92 wt.-%) | 0.2 | 0.2 | 0.2 | 0.2 | 0.2 | 0.2 |

-continued

| Component | Composition 1 | 2 | 3 | 4 | 5 | 6 |
|---|---|---|---|---|---|---|
| | Amount (wt.-%) | | | | | |
| Vanilla aroma, containing 1% Vanillin and 1% of a composition of BDDPA (3 wt.-%) + 2-Phenyl ethanol (47 wt.-%) + Frescolat ® MPC (50 wt.-%) | 0.2 | 0.2 | 0.2 | 0.2 | 0.2 | 0.2 |
| Vanilla aroma, containing 1% Vanillin and 2% of a composition of BDDPA (2 wt.-%) + Frescolat MPC (98 wt.-%) | 0.2 | 0.2 | 0.2 | 0.2 | 0.2 | 0.2 |
| Hesperitin, 2.5% in 1,2-Propylene glycol | 0 | 0.2 | 0 | 0.2 | 0 | 0.2 |

Skimmed mild and glucose syrup were heated to 55° C. and sugar, skimmed milk powder as well as emulsifier were added. The vegetable fat was pre-heated and the total mass was warmed to 58° C. After addition of the aroma, it was homogenized by means of a flow high pressure homogenizer (180/50 bar). The obtained mass was tempered for 1 min at 78° C., subsequently cooled down to 2-4° C. and incubated for maturation at this temperature for 10 hours. Afterwards, the matured mass was filled and stored frozen at −18° C.

Application Example FM-55

Production of sugar containing and sugar-reduced refreshing drinks of different taste directions and a long lasting refreshing coolness impression by using the mixtures according to the invention.

| Component | Amount | Composition 1 | 2 | 3 | 4 | 5 | 6 | 7 | 8 |
|---|---|---|---|---|---|---|---|---|---|
| Saccharose | % | 10.5 | 8 | 8 | 8 | 8 | 8 | 8 | 8 |
| Citric acid | % | 0.2 | 0.2 | 0.2 | 0.2 | 0.2 | 0.2 | 0.2 | 0.2 |
| Hesperetin 1% in 1,2-Propylene glycol | % | | 0.05 | 0.05 | 0.05 | 0.05 | 0.05 | 0.05 | 0.05 |
| Phloretin 1% in 1,2-Propylene glycol | % | | 0.05 | 0.05 | 0.05 | 0.05 | 0.1 | 0.1 | 0.1 |
| Ethylhydroxymethyl furanon | ppb | 0.01 | 0.01 | | | | | | |
| Vanillin | ppb | 15 | 15 | | | | | | |
| Diethyl malonate | ppb | | | 70 | | | | | |
| Phenylethyl acetate | ppb | | | 1 | | | | | |
| 2-Methyl butanal | ppb | | | | 0.3 | | 0.3 | | |
| Isovaleraldehyde | ppb | | | | 0.2 | | 0.2 | | |
| Furfuryl acetate | ppb | | | | 0.3 | | | | |
| Massoilactone | ppb | | | | | 5 | 5 | | 5 |
| γ-Octalactone | ppb | | | | | 5 | 5 | | 5 |
| Ethyl butyrate | ppb | | | | 0.5 | | 0.5 | | 0.5 |
| Maltol | ppb | 350 | 350 | | | | 350 | | 350 |
| 2,5-Dimethyl-4-hydroxy-2H-furan-3-one | ppb | 3 | 3 | | | | 3 | | 3 |
| Ethyl isobutyrate | ppb | | | 0.1 | | | 0.1 | | 0.1 |
| Ethyl-2-methylbutyrate | ppb | | | 0.1 | | | 0.1 | | 0.1 |
| 8 wt.-% BDDPA in 92 wt.-% Benzyl alcohol | ppm | 60 | 60 | 120 | 60 | 60 | 120 | 60 | 120 |
| Butylpheny acetate | ppb | | | | | | 10 | | |
| Acetanisol | ppb | | | | | | 20 | | |
| Methyl sorbate | ppb | | | | | | 100 | | |
| L-Lysin | ppm | | | | | | | 100 | 30 |
| Malonic acid | ppm | | | | | | | 80 | |
| L-Arginine | ppm | | | | | | | 5 | 20 |
| L-Aspartic acid | ppm | | | | | | | 0.5 | |
| Calcium chloride | ppm | | | | | | | 20 | |
| Glutamine | ppm | | | | | | | 2 | |
| Potassium hydrogenphosphate | ppm | | | | | | | 6 | |
| Magnesium chloride | ppm | | | | | | | 20 | |
| L-Valine | ppm | | | | | | | 0.5 | |
| Glycine | ppm | | | | | | | | 40 |
| L-Alanine | ppm | | | | | | | | 20 |
| L-Serine | ppm | | | | | | | | 50 |
| Water | | Ad 100 | | | | | | | |

The substances were provided and filled up to 100% with water and dissolved. The product was, where necessary, filled in bottles and carbonized.

Application Example FM-56

Production of a fruit gum with a long lasting fresh cooling taste by using the cooling substances according to the invention.

| | Composition | | | | | |
|---|---|---|---|---|---|---|
| | 1 | 2 | 3 | 4 | 5 | 6 |
| Component | Amount (wt.-%) | | | | | |
| Water | 23.6 | 23.6 | 23.6 | 23.6 | 23.6 | 23.6 |
| Saccharose | 34.5 | 34.5 | 34.5 | 34.5 | 34.5 | 34.5 |
| Glucose syrup, DE 40 | 31.89 | 31.89 | 31.89 | 31.89 | 31.89 | 31.89 |
| Iso Syrup C* Tru Sweet 01750 (Cerestar GmbH) | 1.5 | 1.5 | 1.5 | 1.5 | 1.5 | 1.5 |
| Gelatine 240 Bloom | 8.2 | 8.2 | 8.2 | 8.2 | 8.2 | 8.2 |
| Yellow and red dye | 0.01 | 0.01 | 0.01 | 0.01 | 0.01 | 0.01 |
| Citric acid | 0.2 | 0.2 | 0.2 | 0.2 | 0.2 | 0.2 |
| Cherry aroma, containing 10 wt.-% of a composition of BDDPA (8 wt.-%) + Benzyl alcohol (92 wt.-%), related to the aroma | 0.1 | | | | | |
| Cherry aroma, containing 10 wt.-% of a composition of BDDPA (2 wt.-%) + Frescolat MPC (98 wt.-%), related to the aroma | | 0.1 | | | | |
| Cherry aroma, containing 5 wt.-% of a composition of BDDPA (5 wt.-%) + Triethyl citrate (47.5 wt.-%) + Peppermint oil (47.5 wt.-%), related to the aroma | | | 0.1 | | | |
| Cherry aroma, containing 5 wt.-% of a composition of BDDPA (5.2 wt.-%) + Triethyl citrate (31.6 wt.-%) + Triacetin (31.6 wt.-%) + Peppermint oil (31.6 wt.-%), related to the aroma | | | | 0.1 | | |
| Cherry aroma, containing 10 wt.-% of a composition of BDDPA (5 wt.-%) + Triacetin (47.5 wt.-%) + Frescolat ® ML (47.5 wt.-%), related to the aroma | | | | | 0.1 | |
| Cherry aroma, containing 10 wt.-% of a composition of BDDPA (3 wt.-%) + 2-Phenyl ethanol (47 wt.-%) + Frescolat ® MPC (50 wt.-%), related to the aroma | | | | | | 0.1 |

Application Example FM-57

Production of sugar containing and sugar-reduced carbonated refreshing drinks of the taste direction "Coke" with a refreshing, long lasting cooling effect by using the mixtures according to the invention.

| | Composition | | | | |
|---|---|---|---|---|---|
| | 1 | 2 | 3 | 4 | 5 |
| Component | Amount (wt.-%) | | | | |
| Phosphoric acid 85% | 0.635 | 0.635 | 0.635 | 0.635 | 0.635 |
| Citric acid, water free | 0.064 | 0.064 | 0.064 | 0.064 | 0.064 |
| Caffeine | 0.064 | 0.064 | 0.064 | 0.064 | 0.064 |
| Succrose | 63.600 | — | — | — | 12.9 |
| Sucralose | — | 0.126 | — | — | — |
| Erythritol | — | — | 6.000 | — | — |
| Aspartame | — | — | 0.350 | — | 0.07 |
| Stevioside | — | — | — | 0.300 | — |
| Acesulfam K | — | — | — | — | 0.07 |
| Caramel | 0.800 | 0.800 | 0.800 | 0.800 | 0.800 |

| Component | Composition | | | | |
|---|---|---|---|---|---|
| | 1 | 2 | 3 | 4 | 5 |
| | Amount (wt.-%) | | | | |
| Drink-Emulsion Type: Cola | 1.445 | 1.445 | 1.445 | 1.445 | 1.445 |
| Sodium benzoate | 0.106 | 0.106 | 0.106 | 0.106 | 0.106 |
| 8 wt.-% BDDPA in 92 wt.-% Benzyl alcohol | 0.30 | 0.15 | | | 0.30 |
| 5 wt.-% BDDPA in 47.5 wt.-% Triethyl citrate + 47.5 wt.-% Peppermint oil | | 0.15 | | | |
| 5.2 wt.-% BDDPA in 31.6 wt.-% Triethyl citrate + 31.6 wt.-% Triacetin + 31.6 wt.-% Peppermint oil | | | 0.30 | | |
| 3 wt.-% BDDPA in 47 wt.-% 2-Phenyl ethanol + 50 wt.-% Frescolat ® MPC | | | | 0.15 | |
| Water | ad 100 | ad 100 | ad 100 | ad 100 | ad 100 |

The solid components or, respectively, ingredients are separately mixed with water, added and filled up to 100 g with water. Subsequently, the obtained concentrate is left over night at room temperature. 1 part of concentrate is mixed with 5 parts of carbonated water, filled in bottles and sealed.

Application Example FM-58

Production of chocolates with a long lasting cooling taste by using the mixtures according to the invention.
1=dark chocolate
2=calorie-reduced dark chocolate
3=calorie-reduced dark chocolate
4=calorie-reduced dark chocolate
5=calorie-reduced whole milk chocolate

| Component | Composition | | | | |
|---|---|---|---|---|---|
| | 1 | 2 | 3 | 4 | 5 |
| | Amount (wt.-%) | | | | |
| Cocoa butter | 13.50 | 13.00 | 13.50 | 9.48 | 14.00 |
| Cocoa mass | 42.00 | 39.00 | 42.00 | 44.00 | 23.00 |
| Erythritol | — | 47.37 | — | — | — |
| Maltitol, crystalline | — | — | — | 22.945 | — |
| Inulin | — | — | — | 23.00 | — |
| Sorbitol | — | — | 43.97 | — | — |
| Lactitol | — | — | — | — | 38.47 |
| Polydextrose | — | — | — | — | 9.70 |
| Whole milk powder | — | — | — | — | 14.0 |
| Sucrose | 43.9 | — | — | — | — |
| Lecitine | 0.48 | 0.48 | 0.40 | 0.48 | 0.50 |
| Vanillin | 0.02 | 0.02 | 0.02 | 0.02 | 0.20 |
| Aspartame | — | 0.03 | 0.06 | — | 0.03 |
| 8 wt.-% BDDPA in 92 wt.-% Benzyl alcohol | 0.1 | 0.1 | | | |
| 2 wt.-% BDDPA in 98 wt.-% Frescolat MPC | | | 0.05 | | |
| 3 wt.-% BDDPA in 47 wt.-% 2-Phenyl ethanol + 50 wt.-% Frescolat ® MPC | | | | 0.075 | 0.1 |

Application Example FM-59

Production of a beer mixture drink with a long lasting fresh cooling taste by using the cooling substances according to the invention
Mixed was:

| Component | Composition | | | | | |
|---|---|---|---|---|---|---|
| | 1 | 2 | 3 | 4 | 5 | 6 |
| | Amount (wt.-%) | | | | | |
| Sugar syrup | 4 | 4 | 4 | 4 | 4 | 4 |
| Beer | 50 | 50 | 50 | 50 | 50 | 50 |
| Ethyl alcohol | 4 | 4 | 4 | 4 | 4 | 4 |
| Citric acid | 0.15 | 0.15 | 0.15 | 0.15 | 0.15 | 0.15 |
| Ascorbic acid | 0.01 | 0.01 | 0.01 | 0.01 | 0.01 | 0.01 |
| Grapefruit juice | 6 | 6 | 6 | 6 | 6 | 6 |
| Grapefruit aroma, containing 5% of a composition of 8 wt.-% BDDPA in 92 wt.-% Benzyl alcohol | 0.2 | | | | | |
| Grapefruit aroma, containing 2% of a composition of 2 wt.-% BDDPA in 98 wt.-% Frescolat MPC | | 0.2 | | | | |

-continued

| Component | Composition | | | | | |
|---|---|---|---|---|---|---|
| | 1 | 2 | 3 | 4 | 5 | 6 |
| | Amount (wt.-%) | | | | | |
| Grapefruit aroma, containing 2% of a composition of 5 wt.-% BDDPA in 47.5 wt.-% Triethyl citrate + 47.5 wt.-% Peppermint oil | | | 0.2 | | | |
| Grapefruit aroma, containing 4% of a composition of 5 wt.-% BDDPA in 47.5 wt.-% Triacetin + 47.5 wt.-% Frescolat ® ML | | | | 0.2 | | |
| Grapefruit aroma, containing 5% of a composition of 3 wt.-% BDDPA in 47 wt.-% 2-Phenyl ethanol + 50 wt.-% Frescolat ® MPC | | | | | 0.2 | |
| Grapefruit aroma, containing 7% of a composition of 5 wt.-% BDDPA in 95 wt.-% Anethol | | | | | | 0.2 |
| Water | ad 100 | ad 100 | ad 100 | ad 100 | ad 100 | ad 100 |
| Carbonic acid | 0.7 | 0.7 | 0.7 | 0.7 | 0.7 | 0.7 |

The effects found in the previous application examples can be transferred to all products of the respective product group, i.e. particularly to toothpastes, chewing gums, mouthwashes, throat lozenges, gelatine capsules, chewing sweets and tea in bags—where necessary by modifications which are easily performed by a person skilled in the art. Due to the present description, it is obvious to the person skilled in the art that the compounds and mixtures—were necessary with minor modifications—can be replaced with each other without due burden. This means that the compound according to the invention used in the products of the application examples have to be perceived as placeholders also for the other compounds and mixtures according to the invention. Also the concentration of the used compound or mixture according to the invention is easily recognizable to be varied. Furthermore, the product specific further components in the respective application example are easily traceable for a person skilled in the art to be replaced or supplemented by further product typical components. A variety of such product typical components are disclosed in the description above.

The following examples clarify the possibilities for application of the cooling substances to be used according to the invention in cosmetic formulations, the use of which may achieve a feeling of coolness perceived as pleasant on the skin and a calming of the skin.

Application Example FM-60 to FM-66

FM-60=Aerosol Deo-Spray
FM-61=Sport Shower Gel
FM-62=After Shave Balm
FM-63=Eau de Toilette
FM-64=Foot Spray
FM-65=Deo Stick
FM-66=Deo APP Roll on Emulsion

| Substance | INCI-Name | Example | | | | | | |
|---|---|---|---|---|---|---|---|---|
| | | FM-60 | FM-61 | FM-62 | FM-63 | FM-64 | FM-65 | FM-66 |
| | | Amount (wt.-%) | | | | | | |
| 8 wt.-% BDDPA in 92 wt.-% Benzyl alcohol | | | | 0.5 | 0.5 | | 0.5 | |
| 2 wt.-% BDDPA in 98 wt.-% Frescolat MPC | | | 0.5 | | | | | 0.5 |
| 5 wt.-% BDDPA in 47.5 wt.-% Triethyl citrate + 47.5 wt.-% Peppermint oil | | 0.5 | | | 0.5 | | | |
| 5.2 wt.-% BDDPA in 31.6 wt.-% Triethyl citrate + 1.6 wt.-% Triacetin + 31.6 wt.-% Peppermint oil | | | 0.5 | 0.1 | | | 0.5 | |
| 5 wt.-% BDDPA in 47.5 wt.-% Triacetin + 47.5 wt.-% Frescolat ® ML | | 0.5 | | | | | | 0.5 |
| 3 wt.-% BDDPA in 47 wt.-% 2-Phenyl ethanol + 50 wt.-% Frescolat ® MPC | | | | | | 0.5 | 0.5 | |
| Allantoin | Allantoin | | | | 0.1 | | | |
| (−) alpha Bisabolol Natural | Bisabolol | | | 0.1 | | | | |

-continued

|  |  | Example ||||||| 
| Substance | INCI-Name | FM-60 | FM-61 | FM-62 | FM-63 | FM-64 | FM-65 | FM-66 |
| --- | --- | --- | --- | --- | --- | --- | --- | --- |
|  |  |  |  | Amount (wt.-%) |||||
| Abil 350 | Dimethicone |  |  |  | 3.0 |  |  |  |
| Akyposoft 100 BVC | Sodium Laureth-11 Carboxylate, Laureth-10 |  | 8.5 |  |  |  |  |  |
| *Aloe Vera* Gel Concentrate 10:1 | *Aloe Barbadensis* Leaf Juice |  |  |  |  |  | 1.0 |  |
| Arlypon F | Laureth-2 |  | 2.5 |  |  |  |  |  |
| Carbopol Ultrez-21 | Acrylates/C10-30 Alkyl Acrylate Crosspolymer |  |  |  | 0.4 |  |  |  |
| Covi-Ox T-70 | Tocopherol |  |  |  | 0.1 |  |  |  |
| Dehyton K | Cocoamidopropyl Betaine |  | 7.0 |  |  |  |  |  |
| Deolite | Dimethyl Phenylpropanol Pentylene Glycol |  |  |  |  |  | 0.5 | 0.5 |
| Dow Corning 246 fluid | Cyclohexasiloxane |  |  |  |  |  |  | 1.0 |
| D-Panthenol 75 L | Panthenol |  |  |  | 1.0 |  |  |  |
| Dracorin ® 100 S.E.P. | Glyceryl Stearate, PEG-100 Stearate |  |  |  |  |  |  | 0.5 |
| Dracorin ® GOC | Glyceryl Oleate Citrate Caprylic Capric Triglyceride |  |  |  |  |  |  | 2.0 |
| Dragocide ® Liquid | Phenoxyethanol, Methylparaben, Ethylparaben, Butylparaben, Propylparaben, Isobutylparaben |  |  | 0.5 | 0.8 |  |  | 0.8 |
| Dragosantol ® 100 | Bisabolol |  |  |  | 0.2 |  | 0.2 | 0.2 |
| Dragoxat ® 89 | Ethylhexyl Isononanoate |  |  |  |  |  | 1.0 |  |
| EDTA BD | Disodium EDTA |  |  |  | 0.1 |  |  |  |
| Ethanol 96% | Ethanol | 26.7 |  |  | 80.15 | 44.1 |  |  |
| Extrapone ®*Ginkgo Biloba* | Propylene Glycol, Water (Aqua), *Ginkgo Biloba* Leaf Extract, Glucose, Lactic Acid |  | 1.0 |  |  |  |  |  |
| Farnesol | Farnesol |  |  |  |  | 0.5 |  |  |
| Fragrance | Perfume | 1.0 | 1.5 | 1.0 | 10.0 | 0.5 | 0.5 | 0.4 |
| Frescolat ® MGA | Menthone Glycerine Acetal |  |  |  |  |  | 0.8 |  |
| Frescolat ® ML | Menthyl Lactate |  | 0.4 | 0.8 |  | 0.2 |  | 0.3 |
| Genapol LRO Liquid | Sodium Laureth Sulfate |  | 39.2 |  |  |  |  |  |
| Glycerine99.5% | Glycerine |  |  |  | 2.5 |  |  | 4.0 |
| Isodragol ® | Triisononanoin |  |  |  |  |  |  | 1.0 |
| Jojoba Oil | *Simmondsia Chinensis* (Jojoba) Seed Oil |  |  |  | 2.0 |  |  |  |
| Sodium Hydroxid 10% Solution | Sodium Hydroxide |  |  | 0.1 | 0.8 |  |  | 0.6 |
| Sodium Stearat | Sodium Stearate |  |  |  |  |  | 9.0 |  |
| Neutral Oil | Caprylic/Capric Triglyceride |  |  |  |  |  |  | 3.5 |
| PCL -Liquid100 | Cetearyl Ethylhexanoate |  |  |  | 3.0 | 1.0 |  |  |
| Pemulen TR-2 | Acrylates/C10-30 Alkyl Acrylate Crosspolymer |  |  |  |  |  |  | 0.3 |
| Polymer JR400 | Polyquaternium-10 |  | 0.3 |  |  |  |  |  |
| Propane Butane 2.7 bar | Propane, Butane | 70.2 |  |  |  | 49.5 |  |  |
| Propylene glycol | Propylene glycol |  |  |  |  |  | 35.7 |  |
| Rezal 36 GP | Aluminium Zirconium Tetrachlorohydrex GLY |  |  |  |  |  |  | 5.0 |

-continued

|  |  | Example | | | | | | |
|---|---|---|---|---|---|---|---|---|
| Substance | INCI-Name | FM-60 | FM-61 | FM-62 | FM-63 | FM-64 | FM-65 | FM-66 |
|  |  | Amount (wt.-%) | | | | | | |
| Solubilizer | PEG-40Hydrogenated Castor Oil, Trideceth-9, Propylene Glycol, Water (Aqua) |  | 0.5 |  | 1.0 | 1.0 |  |  |
| SymAmide UDA | Undecylenamide DEA, Diethanolamine |  |  |  |  | 1.0 |  |  |
| SymCalmin ® | Pentylene Glycol, Butylene Glycol, Hydroxyphenyl Propamidobenzoic Acid |  |  | 0.5 |  |  |  |  |
| SymClariol ® | Decylene Glycol | 0.5 |  |  |  | 0.5 |  |  |
| SymDeo ® MPP | Dimethyl Phenylbutanol | 0.5 |  |  |  |  | 0.5 |  |
| SymMollient ® W/S | Trideceth-9, PEG-5 Isononanoate |  |  |  | 1.0 | 0.5 |  |  |
| SymRelief ® | Bisabolol, *Zingiber Officinale* (Ginger) Root Extract |  | 0.2 | 0.2 |  |  |  |  |
| SymVital ™ | *Aloe Barbadensis* Leaf Juice Powder, Magnesium Ascorbyl Phosphate, *Rubus Idaeus* (Raspberry) Leaf Extract |  |  | 0.1 |  |  |  |  |
| Vitamin E acetat | Tocopherol Acetate |  |  | 0.5 |  |  |  |  |
| Water | Water (Aqua) | ad 100 | ad 100 | ad 100 |  |  | ad 100 | ad 100 |

Application Example FM-67 to FM-72

FM-67=day cream O/W, approx. SPF 15
FM-68=Sun blocker emulsion ca. SPF 25
FM-69=After Sun Spray
FM-70=After Shave
FM-71=Creme W/O
FM-72=Hair Conditioner

|  |  | Examples | | | | | |
|---|---|---|---|---|---|---|---|
| Ingredient | INCI-Name | FM-67 | FM-68 | FM-69 | FM-70 | FM-71 | FM-72 |
|  |  | Amount (wt.-%) | | | | | |
| 8 wt.-% BDDPA in 92 wt.-% Benzyl alcohol |  |  |  | 0.1 | 0.1 |  |  |
| 5 wt.-% BDDPA in 47.5 wt.-% Triethyl citrate + 47.5 wt.-% Peppermint oil |  |  | 0.5 | 0.5 |  | 0.5 | 0.1 |
| 5.2 wt.-% BDDPA in 31.6 wt.-% Triethyl citrate + 31.6 wt.-% Triacetin + 31.6 wt.-% Peppermint oil |  |  |  | 0.25 | 0.2 |  |  |
| 3 wt.-% BDDPA in 47 wt.-% 2-Phenyl ethanol + 50 wt.-% Frescolat ® MPC |  |  |  |  |  | 1 | 1 | 2 |
| Allantoin | Allantoin |  |  |  | 0.1 |  |  |
| (−) alpha Bisabolol Natural | Bisabolol |  |  | 0.2 |  | 0.3 |  |
| Abil 350 | Dimethicone | 2.0 |  |  |  |  |  |
| Aluminium Stearate | Aluminium Stearate |  |  |  |  | 1.2 |  |
| Arlypon F | Laureth-2 |  |  |  |  |  |  |
| Biotive ® L-Arginine | Arginine |  | 0.5 |  |  |  |  |
| Carbopol Ultrez-10 | Carbomer | 0.2 |  | 0.2 |  |  |  |
| Covi-Ox T-70 | Tocopherol |  |  |  | 0.1 |  |  |
| Cutina GMS V | Glyceryl Stearate | 2.0 |  | 2.0 |  |  |  |
| Dehyquart A CA | Cetrimonium chloride |  |  |  |  |  | 4.0 |
| Dow Corning 246 fluid | Cyclohexasiloxane |  |  |  | 2.0 |  |  |
| D-Panthenol 75 L | Panthenol |  |  |  | 1.0 |  | 1.0 |
| Dracorin ® CE | Glyceryl Stearate/Citrate |  | 2.0 |  |  |  |  |

-continued

|  |  | Examples | | | | | |
| --- | --- | --- | --- | --- | --- | --- | --- |
|  |  | FM-67 | FM-68 | FM-69 | FM-70 | FM-71 | FM-72 |
| Ingredient | INCI-Name | | | Amount (wt.-%) | | | |
| Dracorin ® GOC | Glyceryl Oleate Citrate Caprylic Capric Triglyceride |  |  |  | 2.0 |  |  |
| Drago-Beta-Glucan | Water (Aqua), Butylene glycol, Glycerine, *Avena Sativa* (Oat) Kernel Extract |  |  | 2.0 |  |  |  |
| DragoCalm ® | Water, Glycerine, *Avena Sativa* (Oat Kernel Extract) |  |  | 1.0 |  |  |  |
| Dragocide ® Liquid | Phenoxyethanol, Methylparaben, Ethylparaben, Butylparaben, Propylparaben, Isobutylparaben | 0.8 |  |  |  | 0.8 | 0.8 |
| Dragoderm ® | Glycerine, *Triticum Vulgare* (Wheat) Gluten, Water (Aqua) |  |  | 2.0 | 2.0 |  | 2.0 |
| Dragosan W/O P | Sorbitan Isostearate, Hydrogenated Castor Oil, Ceresin, Beeswax (Cera Alba) |  |  |  |  | 8.0 |  |
| Dragosine ® | Carnosine |  |  | 0.2 |  |  |  |
| Dragoxat ® 89 | Ethylhexyl isononanoate |  | 3.0 | 4.0 | 1.0 | 5.0 |  |
| EDTA BD | Disodium EDTA |  | 0.1 | 0.1 |  |  |  |
| Emulsiphos ® | Potassium Cetyl Phosphate, Hydrogenated Palm Glycerides | 2.0 |  | 2.0 |  |  |  |
| Ethanol 96% | Ethanol |  |  |  | 65.0 |  |  |
| Farnesol | Farnesol |  |  |  |  |  |  |
| Fragrance | Perfume | 0.3 | 0.4 | 0.3 | 1.0 | 0.3 | 0.3 |
| Frescolat ® ML | Menthyl Lactate | 0.2 |  |  | 0.3 |  |  |
| Fruitapone ® Orange B | Propylene glycol, Water (Aqua), Citric Acid, *Citrus Aurantium Dulcis* (Orange) Juice, Trideceth-9, Bisabolol | 1.0 |  |  |  |  |  |
| Glycerine99.5% | Glycerine | 2.0 |  | 3.0 | 4.0 | 3.0 |  |
| Hydrolite ®-5 | Pentylene glycol |  | 5.0 |  | 5.0 |  |  |
| Hydroviton ®-24 | Water, Pentylene glycol, Glycerine, Lactic Acid, Sodium Lactate, Serine, Urea, Sorbitol, Sodium Chloride, Allantoin |  |  | 1.0 |  | 2.0 |  |
| Iso Adipat | Diisopropyl adipate |  |  | 1.0 | 5.0 |  |  |
| Jojoba Oil | *Simmondsia Chinensis* (Jojoba) Seed Oil |  |  |  |  | 2.0 |  |
| Keltrol CG RD | Xanthan gum | 0.1 | 0.1 | 0.2 |  |  |  |
| Lanette O | Cetearyl alcohol | 3.0 | 2.0 | 3.0 |  |  | 3.5 |
| Mineral Oil | Mineral oil |  |  |  |  | 8.0 |  |
| Sodium chloride | Sodium chloride |  |  |  |  | 1.0 | 2.0 |

-continued

|  |  | Examples ||||||
|---|---|---|---|---|---|---|---|
|  |  | FM-67 | FM-68 | FM-69 | FM-70 | FM-71 | FM-72 |
| Ingredient | INCI-Name |  |  | Amount (wt.-%) |  |  |  |
| Sodium Hydroxide 10% Solution | Sodium Hydroxide | 0.5 |  |  |  | 0.4 |  |
| Neo Heliopan ® 303 | Octocrylene | 5.0 | 8.0 |  |  |  |  |
| Neo Heliopan ® 357 | Butylmethoxydibenzoylmethane | 1.1 | 3.0 |  |  |  |  |
| Neo Heliopan ® HMS | Homosalate |  | 5.0 |  |  |  |  |
| Neo Heliopan ® Hydro, 25% Solution neutralized with Biotive L-Arginin | Phenylbenzimidazole sulfonic acid | 3.0 | 8.0 |  |  |  |  |
| Neo Heliopan ®AP, 10% Solution, neutralized with NAOH | Disodium phenyl dibenzimidazole tetrasulfonate | 3.0 | 13.3 |  |  |  |  |
| Neo Heliopan ® OS | Ethylhexyl salicylate | 5.0 |  |  |  |  |  |
| Neutral Oil | Caprylic/Capric Triglyceride |  |  |  | 5.0 |  |  |
| Ozokerite Wax 2389 | Ozokerite |  |  |  |  | 2.0 |  |
| Pemulen TR-2 | Acrylates/C10-30 Alkyl Acrylate Crosspolymer |  |  |  | 0.3 |  |  |
| Polyquart H81 | PEG-15 Coco Polyamine |  |  |  |  |  | 3.0 |
| Propylene glycol | Propylene glycol | 3.0 | 4.0 |  |  |  |  |
| Softisan 100 | Hydrogenated Coco Glycerides |  | 1.5 |  |  |  |  |
| Squalan, Vegetable Based | Squalane |  |  | 3.0 |  |  |  |
| SymCalmin ® | Pentylene Glycol, Butylene Glycol, Hydroxyphenyl Propamidobenzoic Acid |  |  | 1.0 |  |  |  |
| SymDiol ® 68 | 1,2 Hexanediol, Caprylyl Glycol |  |  | 1.0 |  |  |  |
| SymGlucan ® | Water (Aqua) Glycerine, Beta Glucan |  |  |  | 1.0 |  |  |
| SymMollient ® W/S | Trideceth-9, PEG-5 Isononanoate |  |  |  | 0.5 |  |  |
| SymRelief ® | Bisabolol, *Zingiber Officinale* (Ginger) Root Extract |  |  |  | 0.2 |  |  |
| SymRepair ® | Hexyldecanol, Bisabolol, Cetylhydroxyproline Palmitamide, Stearic Acid, *Brassica Campestris* (Rapeseed Sterols) |  |  | 2.0 | 3.0 |  |  |
| SymVital ™ | *Aloe Barbadensis* Leaf Juice Powder, Magnesium Ascorbyl Phosphate, *Rubus Idaeus* (Raspberry) Leaf Extract | 0.3 |  |  |  |  |  |
| Triethanolamine 99% | Triethanolamine |  |  | 0.4 | 0.3 |  |  |
| Vitamin E acetate | Tocopherol Acetate |  | 0.5 |  |  | 0.2 |  |
| Water | Water (Aqua) | ad 100 | ad 100 | ad 100 | ad 100 | ad 100 |  |

The invention claimed is:

1. A solution comprising:
   a) 2 to 10 wt. %, based on the total weight of the solution, of solubilized (E)-3-benzo[1,3]dioxol-5-yl-N,N-diphenyl-2-propenamide, and
   b) 90 to 98 wt. %, based on the total weight of the solution, of two or more solvents selected from triethyl citrate, triacetin, and peppermint oil;
   wherein the (E)-3-benzo[1,3]dioxol-5-yl-N,N-diphenyl-2-propenamide is in solution at 23° C.

2. The solution according to claim 1, comprising triethyl citrate and peppermint oil.

3. The solution according to claim 2, comprising triethyl citrate, peppermint oil, and triacetin.

4. A solution consisting of:
   a) 2 to 10 wt. %, based on the total weight of the solution, of solubilized (E)-3-benzo[1,3]dioxol-5-yl-N,N-diphenyl-2-propenamide, and
   b) 90 to 98 wt. %, based on the total weight of the solution, of two or more solvents selected from triethyl citrate, triacetin, peppermint oil, and mixtures thereof.

5. The solution of claim 4 consisting of:
   a) 2 to 10 wt %, based on the total weight of the solution, of solubilized (E)-3-benzo[1,3]dioxol-5-yl-N,N-diphenyl-2-propenamide, and
   b) triethyl citrate and peppermint oil, and
   c) optionally, triacetin.

6. A solution consisting of:
   a) 2 to 10 wt. %, based on the total weight of the solution, of solubilized (E)-3-benzo[1,3]dioxol-5-yl-N,N-diphenyl-2-propenamide, and
   b) 90 to 98 wt. %, based on the total weight of the solution, of triethyl citrate and peppermint oil
   wherein the (E)-3-benzo[1,3]dioxol-5-yl-N,N-diphenyl-2-propenamide is in solution at 23° C.

* * * * *